US012714708B2

(12) United States Patent
Robichaux et al.

(10) Patent No.: US 12,714,708 B2
(45) **Date of Patent: *Aug. 25, 2026**

(54) COMPOUNDS WITH ANTI-TUMOR ACTIVITY AGAINST CANCER CELLS BEARING HER2 EXON 19 MUTATIONS

(71) Applicant: Board of Regents, The University of Texas System, Austin, TX (US)

(72) Inventors: Jacqulyne Robichaux, Houston, TX (US); John V. Heymach, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1028 days.

This patent is subject to a terminal disclaimer.

(21) Appl. No.: 17/042,012

(22) PCT Filed: Mar. 27, 2019

(86) PCT No.: PCT/US2019/024353

§ 371 (c)(1),
(2) Date: Sep. 25, 2020

(87) PCT Pub. No.: WO2019/191279

PCT Pub. Date: Oct. 3, 2019

(65) Prior Publication Data

US 2021/0361655 A1 Nov. 25, 2021

(51) Int. Cl.

*A61K 31/517* (2006.01)
*A61K 45/06* (2006.01)
*A61P 35/00* (2006.01)
*C07K 14/71* (2006.01)
*C12Q 1/6886* (2018.01)

(52) U.S. Cl.

CPC ............ *A61K 31/517* (2013.01); *A61K 45/06* (2013.01); *A61P 35/00* (2018.01); *C07K 14/71* (2013.01); *C12Q 1/6886* (2013.01); *C12Q 2600/106* (2013.01); *C12Q 2600/156* (2013.01)

(58) Field of Classification Search

None
See application file for complete search history.

(56) References Cited

U.S. PATENT DOCUMENTS 8,188,102 B2 5/2012 Lee et al.
11,446,302 B2 * 9/2022 Robichaux .............. A61P 43/00
2002/0177601 A1 11/2002 Himmelsbach et al.
2005/0085495 A1 4/2005 Soyka et al.
2006/0178364 A1 8/2006 Jung et al.
2007/0043009 A1 2/2007 Hennequin et al.
2008/0286785 A1 11/2008 Nishio et al.
2009/0258364 A1 10/2009 Goel et al.
2009/0318480 A1 12/2009 Solca
2011/0142929 A1 6/2011 Messerschmid et al.
2013/0071452 A1 3/2013 Kim et al.
2013/0121996 A1 5/2013 Liu et al.
2014/0112962 A1 4/2014 Kim et al.
2015/0307947 A1 10/2015 Basu et al.
2017/0343554 A1 11/2017 Sullivan et al.
2018/0147279 A1 5/2018 Dar et al.
2018/0333415 A1 11/2018 Potter et al.
2019/0091229 A1 3/2019 Lichenstein et al.
2020/0299783 A1 9/2020 Wang et al.
2020/0316071 A1 10/2020 Robichaux et al.
2020/0370102 A1 * 11/2020 Park ..................... C12Q 1/6841
2021/0235688 A1 8/2021 Tweardy et al.
2021/0361655 A1 11/2021 Robichaux et al.
2022/0041751 A1 2/2022 Heymach et al.
2022/0089620 A1 3/2022 Muller et al.
2022/0143023 A1 5/2022 Robichaux et al.
2022/0143024 A1 5/2022 Andreeff et al.
2022/0163532 A1 5/2022 Sood et al.
2022/0175778 A1 6/2022 Robichaux et al.
2022/0175779 A1 6/2022 Robichaux et al.
2022/0193074 A1 6/2022 Robichaux et al.
2022/0202821 A1 6/2022 Tainer et al.
2022/0305015 A1 9/2022 Hung et al.
2022/0356467 A1 11/2022 Luthra et al.
2023/0233563 A1 7/2023 Robichaux et al.

FOREIGN PATENT DOCUMENTS

EC 03-4464 3/2003
EC 03-4646 7/2003
EC 06-6509 10/2006
EC 07-7645 8/2007
EC 10-10650 12/2010
EC 14-13121 2/2014
JP 2010-529115 8/2010

(Continued)

OTHER PUBLICATIONS

Wen W, Chen WS, Xiao N, Bender R, Ghazalpour A, Tan Z, Swensen J, Millis SZ, Basu G, Gatalica Z, Press MF. Mutations in the Kinase Domain of the HER2/ERBB2 Gene Identified in a Wide Variety of Human Cancers. J Mol Diagn. Sep. 2015;17(5):487-95. (Year: 2015).*

Wang et al. Abstract 4018: Mutations of HER2 at L755 residue results in HER2 nuclear accumulation and enhances breast cancer stem cell activity, AACR Annual Meeting, vol. 78, Iss. 13 Supplement, published Jul. 1, 2018 (Year: 2018).*

Kim et al. "Phase 1 Studies of Poziotinib, an Irreversible Pan-Her Tyrosine Kinase Inhibitor in Patients with Advanced Solid Tumors," Cancer Res Treat. 50(3): 835-842. Published 2017 (Year: 2017).*

Wen et al. Mutations in the Kinase Domain of the HER2/ERBB2 Gene Identified in a Wide Variety of Human Cancers. J Mol Diagn; 17(5):487-95. Published 2015. (Year: 2015).*

Kim et al. Supplemental Tables 2 and 3, Phase 1 Studies of Poziotinib, an Irreversible Pan-Her Tyrposine Kinase Inhibitor in Patients with Solid Tumors Cancer Res Treat, 50(3): 835-842. Published 2017. (Year: 2017).*

(Continued)

*Primary Examiner* — Lauren Wells
(74) *Attorney, Agent, or Firm* — pH IP Law

(57) ABSTRACT

The present disclosure provides methods of treating cancer in a patient determined to have a HER2 exon 19 mutation, such as a point mutation, by administering a third-generation tyrosine kinase inhibitor, such as poziotinib.

18 Claims, 12 Drawing Sheets

Specification includes a Sequence Listing.

(56) References Cited

FOREIGN PATENT DOCUMENTS

| | | | | |
|---|---|---|---|---|
| JP | 2014-513706 | | 6/2014 | |
| JP | 2014-516082 | | 7/2014 | |
| KR | 10-2016-0043114 | A | 4/2016 | |
| WO | WO 2002/018351 | | 3/2002 | |
| WO | WO 2006/091899 | | 8/2006 | |
| WO | WO 2008-150118 | | 12/2008 | |
| WO | WO 2012-156437 | | 11/2012 | |
| WO | WO 2012-169733 | | 12/2012 | |
| WO | WO-2016125169 | A1 * | 8/2016 | ........... A61K 31/145 |
| WO | WO 2017/067447 | | 4/2017 | |
| WO | WO2017/139468 | | 8/2017 | |
| WO | WO 2017/198602 | | 11/2017 | |
| WO | WO 2017/210214 | | 12/2017 | |
| WO | WO 2018/094225 | | 5/2018 | |
| WO | WO 2018/156812 | | 8/2018 | |
| WO | WO 2019-178239 | | 9/2019 | |
| WO | WO 2019/191279 | | 10/2019 | |
| WO | WO 2020/005932 | | 1/2020 | |
| WO | WO 2020/005934 | | 1/2020 | |
| WO | WO 2020/055643 | | 3/2020 | |
| WO | WO2020/132633 | | 6/2020 | |
| WO | WO 2020/150208 | | 7/2020 | |
| WO | WO 2020/205521 | | 10/2020 | |
| WO | WO 2020/205632 | | 10/2020 | |

OTHER PUBLICATIONS

Office Action issued in Japanese Application No. 2020-551912, mailed Jan. 30, 2023, and English translation thereof.

"A phase 1b study of poziotinib in combination with T-DM1 in women with advanced or metastatic HER2-positive breast cancer," Clinical study record (online), US National Library of Medicine, Feb. 12, 2018.

"A phase 2 study of poziotinib in patients with non-small cell lung cancer, locally advanced or metastatic, with EGFR or HER2 exon 20 insertion mutation (POZITIVE20-1)," Clinical study record (online), US National Library of Medicine, Oct. 24, 2017.

"AmoyDx™ EGFR 29 mutations detection kit," technical report by AmoyDx, Apr. 2012.

"Poziotinib in EGFR exon 20 mutant advanced NSCLC," Clinical Trial NCT03066206, Clinical study record (online), US National Library of Medicine, Feb. 28, 2017.

"Vizimpro® (dacomitinib) receives marketing authorization in European Union (EU) for the first-line treatment of adult patients with EGFR-mutated non-small cell lung cancer," Pfizer Inc., Apr. 2019.

An, S-J. et al., "Identification of Enriched Driver Gene Alterations in Subgroups of Non-Small Cell Lung Cancer Patients Based on Histology and Smoking Status," *PLOS ONE*, 7 (2012): 1-8, e40109.

Anido, J. et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells," *Clin Cancer Res*, 9 (2003): 1274-1283.

Arcila, M. E. et al., "EGFR Exon 20 Insertion Mutations in Lung Adenocarcinomas: Prevalence, Molecular Heterogeneity, and Clinicopathologic Characteristics," *Mol Cancer Ther*., 12 (2013): 220-229.

Baselga, J. et al., "Lapatinib with trashtuzumab for HER2-positive early breast cancer (NeoALTTO): a randomized, open-label, multicentre, phase 3 trial," *Lancet*, 379 (2012): 633-640.

Besse, B. et al., "Neratinib (N) with or without Temsirolimus (TEM) in Patients (PTS) with Non-Small Cell Lung Cancer (NSCLC) carrying HER2 Somatic mutations: An International Randomized Phase II Study," *Annals of Oncology*, 25 (2014): abstract.

Callegari, D. et al., "L718Q mutant EGFR escapes covalent inhibition by stabilizing a non-reactive conformation of the lung cancer drug Osimertinib," *Chem Sci*, 9 (2018): 2740-2749.

Cardona, A. F et al., "EGFR exon 20 insertion in lung adenocarcinomas among Hispanics (geno1.2-CLICaP)," *Lung Cancer*, 125 (2018): 265-272.

Chan, A. et al., "Neratinib after trastusumab-based adjuvant therapy in patients with HER2-positive breast cancer (ExteNET): a multicentre, randomized, double-blind, placebo-controlled, phase 3 trial," *The Lancet Oncology*, 17.3 (2016): 367-377.

Cho, J. et al., "Cetuximab response of lung cancer-derived EGF receptor mutants is associated with asymmetric dimerization," *Cancer Res*., 73 (2013): 6770-6779.

Costa, D. B. et al., "Pulse afatinib for ERBB2 exon 20 insertion mutated lung Adenocarcinomas," *J Thorac Oncol*., 11 (2016): 918-923.

Cretella, D. et al. "Trastuzumab emtansine is active on HER-2 overexpressing NSCLC cell lines and overcomes gefitinib resistance," *Molecular Cancer*, 13 (2014): 1-12.

Elamin, Y. et al., "Preliminary Results of a Phase II Study of Poziotinib in EHFR Exon 20 Mutant Advanced NSCLC," *Journal of Thoracic Oncology*, 12 (2017): abstract.

Ettinger, D. S. et al., "NCCN Guidelines Insights: Non-Small Cell Lung Cancer, Version 5.2018," *J Natl Compr Canc Netw*., 16.7 (2018): 807-821.

Extended European Search Report issued in European Application No. 17871141.2, mailed Aug. 31, 2020.

Extended European Search Report issued in European Application No. 20783802.0, mailed Mar. 31, 2023.

Extended European Search Report issued in European Application No. 19899260.4, mailed Nov. 24, 2022.

Extended European Search Report issued in European Application No. 20782979.7, mailed Dec. 6, 2022.

Extended European Search Report issued in European Application No. 20792247.7, mailed Jan. 4, 2023.

Extended European Search Report issued in European Application No. 20790528.2, mailed May 4, 2023.

Fassunke, J. et al., Overcoming EGFR(G724S)-mediated osimertinib resistance through unique binding characteristics of second-generation EGFR inhibitors. *Nature Communications*, 9 (2018): 4655, 1-14.

Gan, H. K. et al., "The epidermal growth factor receptor (EGFR) tyrosine kinase inhibitor AG1478 increases the formation of inactive untethered EGFR dimers. Implications for combination therapy with monoclonal antiboy," *J Bio chem*., 282 (2007): 2840-2850.

Greulich, H. et al., "Functional analysis of receptor tyrosine kinase mutations in lung cancer identifies oncogenic extracellular domain mutations of ERBB2," *Proc Natl Acad Sci U S A*, 109.36 (2012): 14476-14481.

Han, J-Y. et al., "A Phase II Study of Poziotinib in Patients with Epidermal Growth Factor Receptor (EGFR)-Mutant Lung Adenocarcinoma Who Have Acquired Resistance to EGFR-Tyrosine Kinase Inhibitors," *Cancer Res Treat*., 49 (2017): 10-19.

Heymach, J. et al., "A phase II trial of poziotinib in EGFR and HER2 exon 20 mutant non-small cell lung cancer (Nsclc)," *J Thorac Oncol*., 13 (2018): S323-S324.

Hirano, T. et al., "In Vitro modeling to determine mutation specificity of EGFR tyrosine kinase inhibitors against clinically relevant EGFR mutants in non-small-cell lung cancer," *Oncotarget*, 6 (2015): 38789-38803.

Hyman, D. M. et al., "HER kinase inhibition in patients with HER2- and HER3-mutant cancers," *Nature*, 554.7691 (2018): 189-194.

Kim, E. et al., "Metabolite identification of a new tyrosine kinase inhibitor, HM781-36B, and a pharmacokinetic study by liquid chromatography/tandem mass spectrometry," *Rapid Communications in Mass Spectrometry*, 27.11 (2013): 1183-1195.

Kobayashi, Y. et al., "EGFR exon 18 mutations in lung cancer: molecular predictors of augmented sensitivity to afatinib or neratinib as compared with first- or third-generation TKIs," *Clinical Cancer Research*, 21.23 (2015): 5305-5313.

Kobayashi, Y. et al., "Not all epidermal growth factor receptor mutations in lung cancer are created equal: Perspectives for individualized treatment strategy," *Cancer Science*, 107 (2016): 1179-1186.

Kosaka, T. et al., "Response Heterogeneity of EGFR and HER2 Exon 20 Insertions to Covalent EGFR and HER2 Inhibitors," *Cancer Res*, 77 (2017): 2712-2721.

(56) References Cited

OTHER PUBLICATIONS

Le, X. et al., "Landscape of EGFR-dependent and -independent resistance mechanisms to osimertinib and continuation therapy post-progression in EGFR-mutant NSCLC," *Clin Cancer Res*, (2018).
Lee, K. Y. et al., "Molecular Diagnosis in Lung Cancer," *J Lung Cancer*, 9 (2010): 9-14.
Li, B. T. et al., "Ado-trastuzumab emtansine for patients with HER2-mutant lung cancers: results from a phase II basket trial," *J Clin Oncol*, 36 (2018): 2532-2537.
Lynch, T. J. et al., "Activating mutations in the epidermal growth factor receptor underlying responsiveness of non-small-cell lung cancer to gefitinib," *N Engl J Med*, 350.2 (2004): 2129-2139.
Maemondo, M et al., "Gefitinib or Chemotherapy for Non-Small-Cell Lung Cancer with Mutated EGFR," *N Engl J Med*, 362 (2010): 2380-2388.
Mazieres, J. et al., "Crizotinib therapy for advanced lung adenocarcinoma and a ROS1 rearrangement: results from the EUROS1 cohort," *J Clin Oncol*, 33.9 (2015): 992-999.
Mazieres, J. et al., "Lung cancer patients with HER2 mutations treated with chemotherapy and HER2-targeted drugs: results from the European EUHER2 cohort," *Annals of Oncology*, 27 (2016): 281-286.
Mehta, R. et al., "The Role of HER2 Testing in Advanced Colorectal Cancer," *Current Colorectal Cancer Reports*, 14 (2018): 184-191.
Meric-Bernstam, F. et al., "Advances in HER2-Targeted Therapy: Novel Agents and Opportunities Beyond Breast and Gastric Cancer," *Clinical Cancer Research*, 25.7 (2019): 2033-2041.
Mitsudomi, T. et al., "Commentary on EGFR gene mutation examination in lung cancer patients," *EGFR commentary committee of the Japan Lung Cancer Society*, 1 (2009): i-xviii.
Nagano, M. et al., "High-Throughput Functional Evaluation of Variants of Unknown Significance in ERBB2," *Clin Cancer Res*, 24.20 (2018): 5112-5122.
Nam, H-J. et al., "Antitumor activity of HM781-36B, an irreversible Pan-HER inhibitor, alone or in combination with cytotoxic chemotherapeutic agents in gastric cancer," *Cancer Lett.*, 302 (2011): 155-165.
Office Action issued in Australian Patent Application No. 2017363199, mailed Aug. 17, 2022.
Office Action issued in Brazilian Patent Application No. 11 2019 010020-2, mailed Oct. 4, 2022.
Office Action issued in Chilean Office Action 2019-001353, mailed Apr. 20, 2021.
Office Action issued in Chinese Application No. 201780083541.7, mailed Aug. 29, 2022 (English translation).
Office Action issued in Chinese Application No. 201780083541.7, mailed Apr. 13, 2023 (English translation).
Office Action issued in Chinese Patent Application No. 202080032255X, mailed Jul. 15, 2023 (English translation).
Office Action issued in Chinese Patent Application No. 2020800387910, mailed Jun. 30, 2023 (English translation).
Office Action issued in Columbian Application No. NC2019/0006218, mailed Jul. 29, 2022.
Office Action issued in Eurasian Application No. 201991205, mailed Jan. 26, 2021 (English translation).
Office Action issued in Eurasian Application No. 201991205, mailed Aug. 25, 2021 (English translation).
Office Action issued in Eurasian Application No. 201991205, mailed Apr. 22, 2022.
Office Action issued in European Application No. 17871141.2, mailed Jun. 26, 2023.
Office Action issued in Indonesian Application No. P00201904953, mailed Mar. 19, 2021.
Office Action issued in Indonesian Application No. P00201904953, mailed Mar. 31, 2023.
Office Action issued in Japanese Application No. 2019-526282, mailed Dec. 8, 2021 (English translation).
Office Action issued in Japanese Application No. 2019-526282, mailed Sep. 1, 2022 (English translation).
Office Action issued in Korean Application No. 10-2019-7017346, mailed Oct. 31, 2022 (English translation).
Office Action issued in Korean Application No. 10-2019-7017346, mailed Mar. 20, 2023 (English translation).
Office Action issued in Korean Application No. 10-2019-7017346, mailed Jun. 27, 2023.
Office Action issued in Mexican Application No. MX/a/2019/005824, mailed May 20, 2021 (English translation).
Office Action issued in Mexican Application No. MX/a/2019/005824, mailed Jan. 19, 2022 (English translation).
Office Action issued in Russian Application No. 2021131360, mailed Dec. 7, 2021.
Office Action issued in Taiwanese Application No. 106139967, mailed Feb. 21, 2022 (English translation).
Opposition filed in Ecuadoran Application No. 2019-43254, mailed Feb. 5, 2020. (English translation).
Paez, J. G. et al., "EGFR mutations in lung cancer: correlation with clinical response to gefitinib therapy," *Science*, 304.5676 (2004): 1497-1500.
Pan, Y. et al., "Prevalence, Clinicopathologic Characteristics, and Molecular Associations of EGFR Exon 20 Insertion Mutations in East Asian Patients with Lung Adenocarcinoma," *Annals of Surgical Oncology*, 21 (2014): S490-S496.
Pao, W. et al., "EGF receptor gene mutations are common in lung cancers from "never smokers" and are associated with sensitivity of tumors to gefitinib and erlotinib," *Proc Natl Acad Sci USA*, 7.101 (2004): 13306-13311.
Papadimitrakopoulou, V. A. et al., "Everolimus and Erlotinib as Second- or Third-Line Therapy in Patients with Advanced Non-Small-Cell Lung Cancer," *Journal of Thoracic Oncology*, 7 (2012): 1594-1601.
PCT International Preliminary Report on Patentability issued in International Application No. PCT/US2020/025228, mailed Oct. 14, 2021.
PCT International Preliminary Report on Patentability issued in International Application No. PCT/US2017/062326, mailed May 31, 2019.
PCT International Preliminary Report on Patentability issued in International Application No. PCT/US2019/068153, mailed Jul. 1, 2021.
PCT International Preliminary Report on Patentability issued in International Application No. PCT/US2020/025478, mailed Oct. 14, 2021.
PCT International Preliminary Report on Patentability issued in International Application No. PCT/US2020/028540, mailed Oct. 28, 2021.
PCT International Preliminary Report on Patentability issued in International Application No. PCT/US2020/028547, mailed Oct. 28, 2021.
PCT International Search Report and Written Opinion issued in International Application No. PCT/US2020/025228, mailed Jul. 22, 2020.
PCT International Search Report and Written Opinion issued in International Application No. PCT/US2017/062326, mailed Mar. 29, 2018.
PCT International Search Report and Written Opinion issued in International Application No. PCT/US2019/068153, mailed Apr. 14, 2020.
PCT International Search Report and Written Opinion issued in International Application No. PCT/US2020/025478, mailed Aug. 27, 2020.
PCT International Search Report and Written Opinion issued in International Application No. PCT/US2020/028540, mailed Jul. 8, 2020.
PCT International Search Report issued in International Application No. PCT/US2020/028547, mailed Jul. 22, 2020.
Robichaux, J. et al., "MA16.07 Drug Repurposing to Overcome De Novo Resistance of Non-Traditional EGFR Mutations," *Journal of Thoracic Oncology*, 12 (2017): S438.
Robichaux, J. P. et al., "Inhibition of HER2 mutant non-small cell lung cancer using 3rd generation EGFR/HER2 inhibitors," *Cancer Res*, 76 (2016) (14 Supplement): 4799.

(56) References Cited

OTHER PUBLICATIONS

Russo, A. et al., "Heterogeneous Responses to Epidermal Growth Factor Receptor (EGFR) Tyrosine Kinase Inhibitors (TKIs) in Patients with Uncommon EGFR Mutations: New Insights and Future Perspectives in this Complex Clinical Scenario," *International Journal of Molecular Sciences*, 20 (2019): 1431, 1-20.

Scaltriti, M. et al., "Lapatinib, a HER2 tyrosine kinase inhibitor, induces stabilization and accumulation of HER2 and potentiates trastuzumab-dependent cell cytotoxicity," Oncogene, 28 (2009): 803-814.

Search Report issued in Singapore Patent Application No. 11202109531U, issued Jul. 20, 2023.

Search Report issued in Singapore Patent Application No. 11202111120V, issued Aug. 22, 2023.

Soria, J. C. et al., "Osimertinib in Untreated EGFR-Mutated Advanced Non-Small-Cell Lung Cancer," *N Engl J Med*, 378.2 (2018): 113-125.

Suzawa, K. et al., "Antitumor effect of afatinib, as a human epidermal growth factor receptor 2-targeted therapy, in lung cancers harboring HER2 oncogene alterations," *Cancer Science*, 107 (2016): 45-52.

Thress, K. S. et al., "Acquired EGFR C797S mutation mediates resistance to AZD9291 in non-small cell lung cancer harboring EGFR T790M," *Nat Med*., 21 (2015): 560-562.

Van Der Steen, N. et al., "Resistance to epidermal growth factor receptor inhibition in non-small cell lung cancer," *Cancer Drug Resistance*, 1 (2018): 230-249.

Vogel, C. L. et al., "Efficacy and safety of trastuzumab as a single agent in first-line treatment of HER2-overexpressing metastatic breast cancer," *J Clin Oncol*., 20.3 (2002): 719-726.

Vyse, S. et al., "Targeting EGFR exon 20 insertion mutations in non-small cell lung cancer," *Signal Transduction and Targeted Therapy*, 4.1(2019): 1-10.

Wen, W. et al., "Mutations in the Kinase Domain of the HER2/ERBB2 Gene Identified in a Wide Variety of Human Cancers," *The Journal of Molecular Diagnostics*, 17 (2015): 487-495.

Woo, H. S. et al., "Epidermal growth factor receptor (EGFR) exon 20 mutations in non-small-cell lung cancer and resistance to EGFR-tyrosine kinase inhibitors," *Investigational New Drugs*, 32 (2014): 1311-1315.

Xu, Z.-q. et al., "Efficacy and safety of lapatinib and trustuzumab for HER2-positive breast cancer: a systematic review and meta-analysis of randomized controlled trials," *BMJ Open*, 7 (2017): e013053, 1-9.

Yang et al. "Clinical activity of afatinib inpatients with advanced non-small-cell lung cancer harbouring uncommon EGFR mutations: a combined post-hoc analysis of LUX-Lung 2, LUX-Lung 3, and LUX-Lung 6," *The Lancet Oncology*, 16 (2015): 830-838.

Yang, C-Y. et al., "Programmed cell death-ligand 1 expression is associated with a favourable immune microenvironment and better overall survival in stage I pulmonary squamous cell carcinoma," *Eur J Cancer*, 57 (2016): 91-103.

Yang, M. et al., "NSCLC harboring EGFR exon-20 insertions after the regulatory C-helix of kinase domain responds poorly to known EGFR inhibitors," *Int. J. Cancer*, 139 (2016): 171-176.

Yasuda, H. et al., "EGFR exon 20 insertion mutations in non-small-cell lung cancer: preclinical data and clinical implications," *Lancet Oncol*, 13 (2012): e23-31.

Yasuda, H. et al., "Structural, biochemical and clinical characterization of epidermal growth factor receptor (EGFR) exon 20 insertion mutations in lung cancer," *Sci Transl Med*, 5 (2013): 1-23.

Yu, X. et al., "First-generation EGFR tyrosine kinase inhibitor therapy in 106 patients with compound EGFR-mutated lung cancer: a single institution's clinical practice experience," *Cancer Communication*, 38 (2018): 1-13.

Kim et al., "Phase 1 studies of Poziotinib, an irreversible Pan-HER tyrosine kinase inhibitor in patients with advanced solid tumors," *Cancer Res Treat*., 50(3):835-842, 2018.

Office Action issued in Chinese Application No. 201980022143.3, mailed Feb. 22, 2023, and English translation thereof.

Arcila et al., "Prevalence, clinicopathologic associations, and molecular spectrum of ERBB2 (HER2) tyrosine kinase mutations in lung adenocarcinomas", Clin Cancer Res, 18:4910-8 (2012).

Bose et al., "Activating HER2 Mutations in HER2 Gene Amplification Negative Breast Cancer", Cancer Discovery, vol. 3, No. 2, pp. 224-237, Feb. 1, 2013.

Cha et al., "Antitumor activity of HM781-36B, a highly effective pan-HER inhibitor in erlotinib-resistant NSCLC and other EGFR-dependent cancer models", Int. J. of Cancer, 130, 2445-2454 (2012).

De Greve et al., "Clinical activity of afatinib (BIBW 2992) in patients with lung adenocarcinoma with mutations in the kinase domain of HER2/neu", Lung Cancer, 76:123-7 (2012).

International Preliminary Report on Patentability for PCT/US2019/024353 dated Sep. 29, 2020, 14 pages.

International Search Report and Written Opinion for PCT/US2019/024353 dated Oct. 1, 2019, 20 pages.

Kamitani et al., "Mutations in transmembrane domain of carbB-2 gene in human malignant tumours of the central nervous system", Neurological Research, vol. 14, No. 3, pp. 236-240, Jun. 1992.

Kim et al., "Phase I study of HM781-36B, an irreversible pan-HER tyrosine kinase inhibitor (TKI) in patients with advanced solid tumor and the therapeutic potential in patients with advanced non-small cell lung cancer (NSCLC)", Abstract #2029, Department of Internal Medicine, Seoul National University Hospital Seoul/Korea (2013).

Kris et al, "Targeting HER2 aberrations as actionable drivers in lung cancers: phase II trial of the pan-HER tyrosine kinase inhibitor dacomitinib in patients with HER2-mutant or amplified tumors", Ann Oncol, 26:1421-7 (2015).

Mazieres et al., "Lung cancer that harbors an HER2 mutation: epidemiologic characteristics and therapeutic perspectives", J. Clin Oncol, 31:1997-2003 (2013).

Mitsudomi and Yatabe, "Mutations of the epidermal growth factor receptor gene and related genes as determinants of epidermal growth factor receptor tyrosine kinase inhibitors sensitivity in lung cancer", Cancer Sci. 98(12):1817-1824, (2007).

Ou et al., "HER2 Transmembrane Domain (TMD) Mutations (V659/G660) That Stabilize Homo- and Heterodimerization Are Rare Oncogenic Drivers in Lung Adenocarcinoma That Respond to Afatinib", J. Thorac Oncol., vol. 12, No. 3, pp. 446-457, Mar. 2017.

Park et al., "A phase II trial of pan-HER inhibitor Poziotinib, in patients with HER2-positive metastatic breast cancer who have received at least two prior HER2-directed regimens: The results of Nov120101-203 trial", Annals of Oncology, vol. 28, Suppl. 5, p. v74, Sep. 1, 2017.

Perera et al., "HER2$^{YVMA}$ drives rapid development of adenosquamous lung tumors in mice that are sensitive to BIBW2992 and rapamycin combination therapy", Proc Natl Acad Sci U S A 106:474-9, 2009.

Robichaux et al., "Pan-Cancer Landscape and Analysis of ERBB2 Mutations Identifies Poziotinib as a Clinically Active Inhibitor and Enhancer of T-DM1 Activity", Cancel Cell, vol. 36, No. 4, p. 444, Oct. 3, 2019.

Robichaux et al., "Mechanisms and Clinical Activity of an EGFR and HER2 Exon 20-selective Kinase Inhibitor in Non-small Cell Lung Cancer", Nature Medicine, 2018.

Singapore Search Report for Application No. 11202009498R dated Jun. 29, 2022, 11 pages.

Sun et al., "Analysis of different HER-2 mutations in breast cancer progression and drug resistance", J. Cell. Mol. Med., vol. 19, No. 12, pp. 2691-2701, 2015.

Supplementary European Search Report for EP19775368, dated Feb. 23, 2022, 13 pages.

Supplementary Partial European Search Report for EP19775368, dated Nov. 21, 2021, 13 pages.

Wang et al., "HER2 kinase domain mutation results in constitutive phosphorylation and activation of HER2 and EGFR and resistance to EGFR tyrosine kinase inhibitors", Cancer Cell, 10:25-38 (2006).

Yang et al., "Atomistic insights into the lung cancer-associated L755P mutation in HER2 resistance to lapatinib: a molecular dynamics study", J. Jol Model, 21:24 (2015).

(56) References Cited

OTHER PUBLICATIONS

Castellano et al., "A novel acquired exon 20 EGFR M766Q mutation in lung adenocarcinoma mediates osimertinib resistance but is sensitive to neratinib and poziotinib," *Journal of Thoracic Oncology*, 14(11):1982-1988, 2019.
Koga et al., "Activity of a novel HER2 inhibitor, poziotinib, for HER2 exon 20 mutations in lung cancer and mechanism of acquired resistance: an in vitro study," *Lung Cancer*, 126:72-79, 2018.
Le et al., "Poziotinib in non-small-cell lung cancer harboring HER2 exon 20 insertion mutations after ZENITH20-2 trial," *Journal of Clinical Oncology*, 40(7):710-718, 2021.
Prelaj et al., "Poziotinib for EGFR and HER2 exon 20 insertion mutation in advanced NSCLC: results from the expanded access program," *European Journal of Cancer*, 149:235-248, 2021.
Translation of Japanese Application No. JP 2020-502059, filed Nov. 17, 2017.
Udagawa et al., "Clinical outcome of non-small cell lung cancer with EGFR/HER2 exon 20 insertions identified in the LC-SCRUM-Japan," *Journal of Thoracic Oncology*, 14(10S):S224, OA07.03, 2019.

* cited by examiner

| | $IC_{50}$ (nM) |
|---|---|
| Trastuzumab | >10,000 |
| Lapatinib | 3,000 |
| Afatinib | 13 |
| EGF 816 | 75 |
| Ibrutinib | 308 |
| Poziotinib | 3 |

| IC50, nM | Sapatinib | Lapatinib | Afatinib | Dacomitinib | Neratinib |
|---|---|---|---|---|---|
| HER2 L755S | 376.30 | 96.34 | 4.37 | 12.49 | 3.28 |
| HER2 L755P | 587.25 | 474.68 | 27.15 | 25.16 | 19.71 |
| HER2 D769H | 231.00 | 31.66 | 2.71 | 7.04 | 2.50 |
| HER2 D769N | 83.79 | 1.76 | 0.81 | 2.65 | 0.51 |
| HER2 D769Y | 58.15 | 8.68 | 1.48 | 3.67 | 1.02 |

| Tarloxotinib-TKI | Poziotinib | Pyrotinib | Ibrutinib | Osimertinib | Nazartinib |
|---|---|---|---|---|---|
| 3.67 | 0.53 | 41.60 | 51.54 | 12.41 | 23.48 |
| 5.61 | 3.65 | 55.18 | 190.24 | 69.58 | 68.99 |
| 0.57 | 0.35 | 5.36 | 7.38 | 13.80 | 35.55 |
| 0.93 | 0.12 | 4.53 | 3.74 | 8.10 | 10.10 |
| 0.59 | 0.36 | 0.78 | 6.68 | 7.38 | 23.13 |

SEQUENCE LISTING

```
<160> NUMBER OF SEQ ID NOS: 1

<210> SEQ ID NO 1
<211> LENGTH: 102
<212> TYPE: PRT
<213> ORGANISM: Homo sapiens

<400> SEQUENCE: 1

Gly Val Val Phe Gly Ile Leu Ile Lys Arg Arg Gln Gln Lys Ile Arg
1               5                   10                  15

Lys Tyr Thr Met Arg Arg Leu Leu Gln Glu Thr Glu Leu Val Glu Pro
            20                  25                  30

Leu Thr Pro Ser Gly Ala Met Pro Asn Gln Ala Gln Met Arg Ile Leu
        35                  40                  45

Lys Glu Thr Glu Leu Arg Lys Val Lys Val Leu Gly Ser Gly Ala Phe
    50                  55                  60

Gly Thr Val Tyr Lys Gly Ile Trp Ile Pro Asp Gly Glu Asn Val Lys
65                  70                  75                  80

Ile Pro Val Ala Ile Lys Val Leu Arg Glu Asn Thr Ser Pro Lys Ala
                85                  90                  95

Asn Lys Glu Ile Leu Asp
            100
```

COMPOUNDS WITH ANTI-TUMOR ACTIVITY AGAINST CANCER CELLS BEARING HER2 EXON 19 MUTATIONS

This invention was made with government support under grant number CA190628 awarded by the National Institutes of Health. The government has certain rights in the invention.

This application is a national phase application under 35 U.S.C. § 371 of International Application No. PCT/US2019/024353, filed Mar. 27, 2019, which claims the benefit of U.S. Provisional Patent Application No. 62/648,629, filed Mar. 27, 2018 and 62/688,049 filed Jun. 21, 2018, each of which is incorporated herein by reference in its entirety.

INCORPORATION OF SEQUENCE LISTING

The sequence listing that is contained in the file named "UTFC.P1354WOWO_ST25" which is 1.3 KB (as measured in Microsoft Windows®) and was created on Mar. 27, 2019, is filed herewith by electronic submission and is incorporated by reference herein.

BACKGROUND

1. Field

The present invention relates generally to the field of molecular biology and medicine. More particularly, it concerns methods of treating patients with HER2 exon 19 mutations, such as point mutations.

2. Description of Related Art

HER2 is mutated in 2-3% of non-small cell lung cancer (NSCLC) cases, and tyrosine kinase inhibitors (TKIs) with activity against HER2 including afatinib and dacomitinib have yielded objective response rates less than 30%. Although the majority of HER2 mutations in NSCLC occur within exon 20, point mutations within exon 19 occur in NSCLC and other cancers such as breast cancer. Previous studies have shown that point mutations in exon 19 of HER2 are often resistant to currently approved tyrosine kinase inhibitors such as lapatinib due to a less energetically favorable HER2/drug complex. Therefore, there is a significant clinical need to identify novel therapies to overcome the innate drug resistance of NSCLC tumors harboring HER exon 19 mutations.

SUMMARY

In certain embodiments, the present disclosure provides methods and compositions for treating cancer in patients with HER2 exon 19 mutations, such as exon 19 point mutations. In one embodiment, there is provided a method of treating cancer in a subject comprising administering an effective amount of poziotinib to the subject, wherein the subject has been determined to have one or more HER2 exon 19 mutations, such as one or more HER2 exon 19 point mutations. In particular aspects, the subject is human.

In certain aspects, the one or more HER exon 19 mutations comprise one or more point mutations, insertions, and/or deletions of 1-18 nucleotides between amino acids 668-769 of HER2 (e.g., SEQ ID NO:1). In some aspects, the subject has been determined to have 2, 3, or 4 HER2 exon 19 mutations. In some aspects, the one or more HER2 exon 19 mutations are at one or more residues selected from the group consisting of R668, R678, V754, L755, I767 and D769. In some aspects, the one or more HER2 exon 19 mutations are selected from the group consisting of R668Q, R678Q, V754M, L755P, L755S, L755W, D769H, D769N, I767M, and D769Y. In some aspects, the one or more HER2 exon 19 mutations are at one or more residues selected from the group consisting of R668, R678, V754, L755, and D769. In some aspects, the one or more HER2 exon 19 mutations are selected from the group consisting of R668Q, R678Q, V754M, L755P, L755S, L755W, D769H, D769N, and D769Y.

In some aspects, the poziotinib is further defined as poziotinib hydrochloride salt. In certain aspects, the poziotinib hydrochloride salt is formulated as a tablet.

In some aspects, the subject is resistant or has shown resistance to the previously administered tyrosine kinase inhibitor. In certain aspects, the tyrosine kinase inhibitor is lapatinib, afatinib, dacomitinib, osimertinib, ibrutinib, nazartinib, or beratinib.

In certain aspects, the poziotinib is administered orally. In some aspects, the poziotinib is administered at a dose of 5-25 mg, such as 6, 7, 8, 9, 10, 11, 12, 13, 14, 15, 16, 17, 18, 19, 20, 21, 2, 23, 24, or 25 mg. In certain aspects, the poziotinib is administered at a dose of 8 mg, 12 mg, or 16 mg. In some aspects, the poziotinib is administered daily. In certain aspects, the poziotinib is administered on a continuous basis. In some aspects, the poziotinib is administered on 28 day cycles.

In certain aspects, the subject was determined to have a HER2 exon 19 mutation, such as a point mutation, by analyzing a genomic sample from the subject. In some aspects, the genomic sample is isolated from saliva, blood, urine, normal tissue, or tumor tissue. In particular aspects, the presence of an HER exon 19 mutation is determined by nucleic acid sequencing (e.g., DNA sequencing of tumor tissue or circulating free DNA from plasma) or PCR analyses.

In certain aspects, the method further comprises administering an additional anti-cancer therapy. In some aspects, the anti-cancer therapy is chemotherapy, radiotherapy, gene therapy, surgery, hormonal therapy, anti-angiogenic therapy or immunotherapy. In certain aspects, the poziotinib and/or anti-cancer therapy are administered intravenously, subcutaneously, intraosseously, orally, transdermally, in sustained release, in controlled release, in delayed release, as a suppository, or sublingually. In some aspects, administering the poziotinib and/or anti-cancer therapy comprises local, regional or systemic administration. In particular aspects, the poziotinib and/or anti-cancer therapy are administered two or more times, such as daily, every other day, or weekly.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In some aspects, the cancer is lung cancer, breast cancer, bladder cancer, anal cancer, endometrial cancer, ovarian cancer, or non-small cell lung cancer (NSCLC). In particular aspects, the cancer is NSCLC.

In another embodiment, there is provided a pharmaceutical composition comprising poziotinib for a patient determined to have one or more HER2 exon 19 mutations, such as one or more HER2 exon 19 point mutations. In certain aspects, the one or more HER exon 19 mutations comprise a point mutation, insertion, and/or deletion of 1-18 nucleotides between amino acids 668-769. In certain aspects, the subject has been determined to have 2, 3, or 4 HER2 exon 19 mutations.

In some aspects, the one or more HER2 exon 19 mutations are at one or more residues selected from the group consisting of R668, R678, V754, L755, I767 and D769. In particular aspects, the one or more exon 19 mutations are selected from the group consisting of R668Q, R678Q, V754M, L755P, L755S, L755W, D769H, D769N, I767M, and D769Y. In some aspects, the patient is being treated with an anti-cancer therapy. In some aspects, the one or more HER2 exon 19 mutations are at one or more residues selected from the group consisting of R668, R678, V754, L755, and D769. In some aspects, the one or more HER2 exon 19 mutations are selected from the group consisting of R668Q, R678Q, V754M, L755P, L755S, L755W, D769H, D769N, and D769Y.

In yet another embodiment, there is provided a method of predicting a response to poziotinib alone or in combination with an anti-cancer therapy in a subject having a cancer comprising detecting an HER2 exon 19 mutation (e.g., HER2 exon 19 point mutation) in a genomic sample obtained from said patient, wherein if the sample is positive for the presence of the HER2 exon 19 mutation, then the patient is predicted to have a favorable response to poziotinib alone or in combination with an anti-cancer therapy. In some aspects, the genomic sample is isolated from saliva, blood, urine, normal tissue, or tumor tissue. In certain aspects, the presence of an HER2 exon 19 mutation is determined by nucleic acid sequencing or PCR analyses. In certain aspects, the HER2 exon 19 mutation comprises one or more point mutations, insertions, and/or deletions of 1-18 nucleotides between amino acids 668-769. In some aspects, the HER2 exon 19 mutation is at residue R668, R678, V754, L755, I767, and D769. In some aspects, the EGFR exon 19 mutation is selected from the group consisting of R668Q, R678Q, V754M, L755P, L755S, L755W, D769H, D769N, I767M and D769Y. In some aspects, the one or more HER2 exon 19 mutations are at one or more residues selected from the group consisting of R668, R678, V754, L755, and D769. In some aspects, the one or more HER2 exon 19 mutations are selected from the group consisting of R668Q, R678Q, V754M, L755P, L755S, L755W, D769H, D769N, and D769Y. In certain aspects, a favorable response to poziotinib inhibitor alone or in combination with an anti-cancer therapy comprises reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, or increased patient survival. In further aspects, the patient predicted to have a favorable response is administered poziotinib alone or in combination with a second anti-cancer therapy.

In another embodiment, there is provided an isolated nucleic acid encoding a mutant HER2 protein, wherein said mutant protein differs from wild-type human HER2 by one or more HER2 exon 19 mutations comprising a point mutation, insertion, and/or deletion of 1-18 nucleotides between amino acids 668-769 of HER2 or SEQ ID NO:1 (GVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILD). In some aspects, the one or more HER2 exon 19 mutations are at one or more residues selected from the group consisting of R668, R678, V754, L755, I767, and D769. In certain aspects, the one or more exon 19 mutations are selected from the group consisting of R668Q, R678Q, V754M, L755P, L755S, L755W, D769H, D769N, I767M, and D769Y. In some aspects, the one or more HER2 exon 19 mutations are at one or more residues selected from the group consisting of R668, R678, V754, L755, and D769. In some aspects, the one or more HER2 exon 19 mutations are selected from the group consisting of R668Q, R678Q, V754M, L755P, L755S, L755W, D769H, D769N, and D769Y. In some aspects, the method further comprises administering poziotinib alone or in combination with a second anti-cancer therapy to said patient predicted to have a favorable response.

Further provided herein is a composition comprising nucleic acids isolated from human cancer cells; and a primer pair that can amplify at least a first portion of mutated exon 19 of a human HER2 coding sequence.

In some aspects, the composition further comprises a labeled probe molecule that can specifically hybridize to the first portion of exon 19 of the human HER coding sequence when there is a mutation in the sequence. In certain aspects, the composition further comprises a thermostable DNA polymerase. In certain aspects, the composition further comprising dNTPS. In particular aspects, the labeled probe hybridizes to the first portion of exon 19 of the human HER2 coding sequence when there is a mutation selected from the group consisting of R668Q, R678Q, V754M, L755P, L755S, L755W, D769H, D769N, and D769Y.

A further embodiment provides an isolated nucleic acid encoding a mutant HER2 protein, wherein said mutant protein differs from wild-type human HER2 by one or more HER2 exon 19 mutations comprising one or more point mutations, insertions, and/or deletions of 1-18 nucleotides between amino acids 668-769. In some aspects, the one or more HER2 exon 19 mutations are at residue R668, R678, V754, L755, I767 and/or D769. In certain aspects, the one or more HER2 exon 19 mutations are selected from the group consisting of R668Q, R678Q, V754M, L755P, L755S, L755W, D769H, D769N, I767M, and D769Y. In some aspects, the one or more HER2 exon 19 mutations are at one or more residues selected from the group consisting of R668, R678, V754, L755, and D769. In some aspects, the one or more HER2 exon 19 mutations are selected from the group consisting of R668Q, R678Q, V754M, L755P, L755S, L755W, D769H, D769N, and D769Y.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-5D: (A) Heatmap of log $IC_{50}$ values of Ba/F3 cells stably expressing the indicated mutations after 72 hours of drug treatment. Cell viability was determined by the Cell Titer Glo assay (N≥3). (B), Average $IC_{50}$ HER2 exon 19 mutant cell lines after drug treatment for 72 hours. Bars are representative of mean±SEM (N≥3). (C) Average $IC_{50}$ values of Ba/F3 cells expressing L755S or L755P with indicated inhibitors. Dots are representative of mean±SEM (N≥3). Statistical significance was determined by a paired t-test. (D) Table of IC50 values for each drug and mutation represented in panel A heatmap.

DESCRIPTION OF ILLUSTRATIVE EMBODIMENTS

Figure 1A:
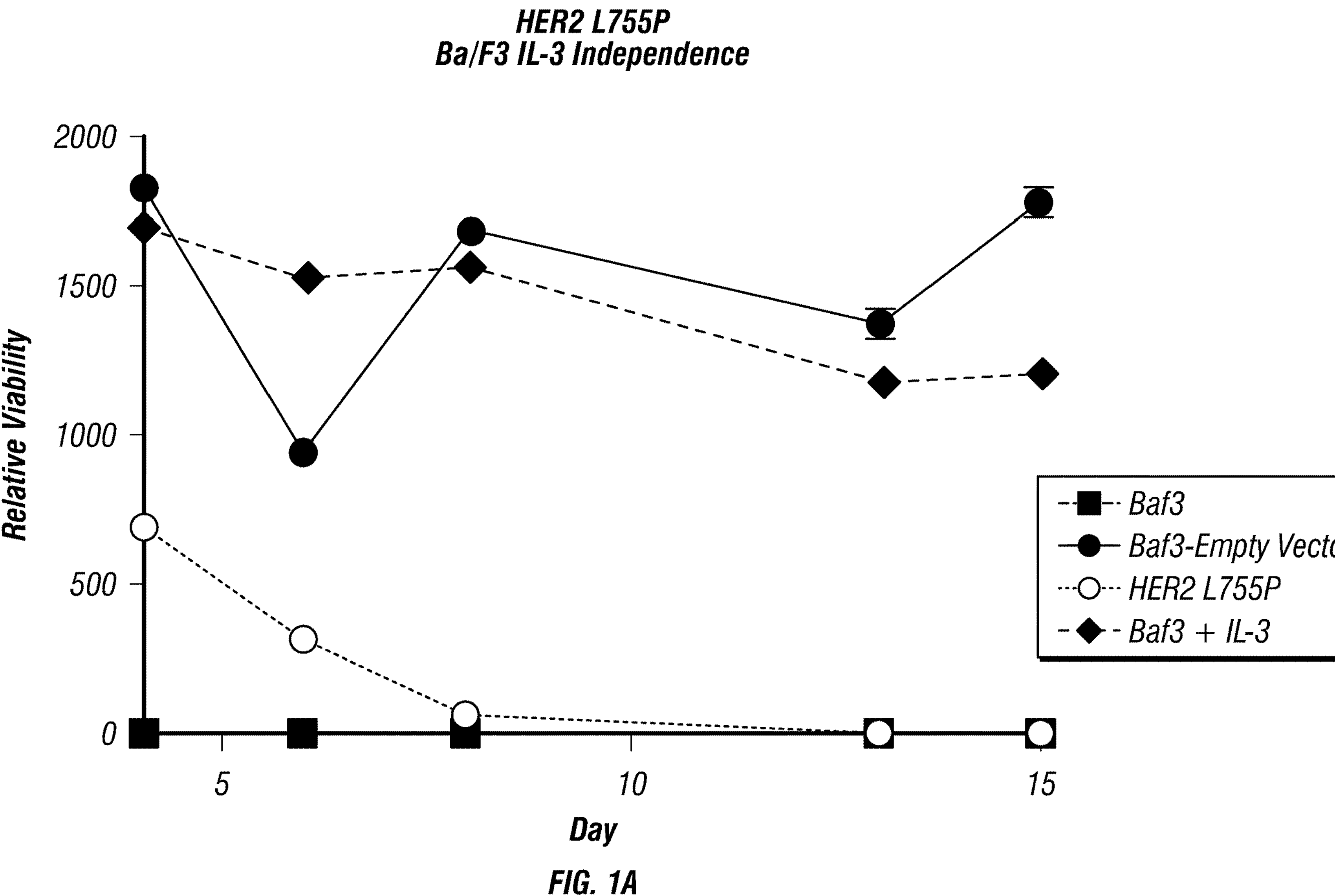
FIGS. 1A-1B: IL-3 independent growth of stable-Ba/F3 cell lines expressing empty vector or HER2 L755P demonstrate that L755P is an activating HER2 mutation. Cell viability was determined by the Cell Titer Glo assay. The mean±SEM is plotted for each cell line (n=3). Dose response curves of HER2 L755P Ba/F3 cells treated with indicated inhibitors demonstrate inhibition of cell viability by poziotinib. Cell viability was determined by the Cell Titer Glow assay over time (FIG. 1A), and $IC_{50}$ estimations were calculated by GraphPad Prism (FIG. 1B). The mean±SEM is plotted for each dose n=2.
Figure 1B:
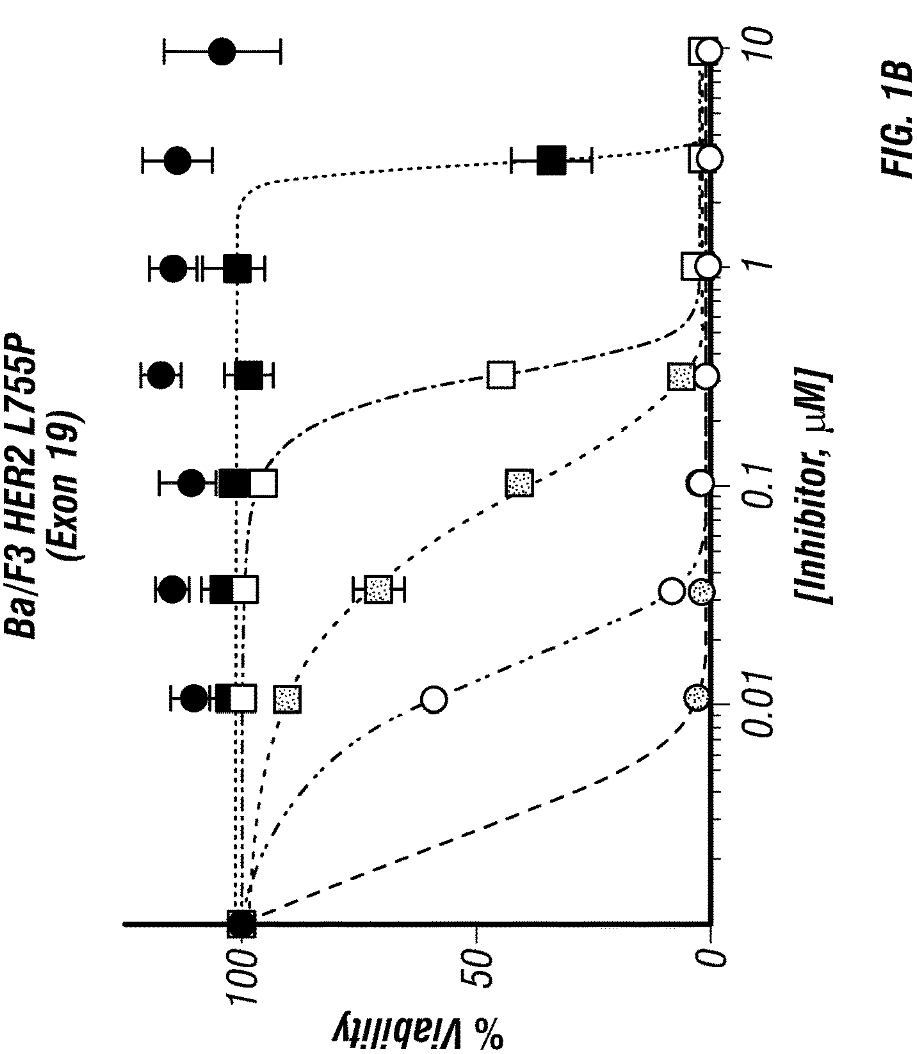

Although the majority of activating mutations of HER2 mutant non-small cell lung cancers (NSCLCs) are sensitive to available EGFR tyrosine kinase inhibitor (TKIs), a subset with alterations in exon 19 of HER2 are resistant. The present studies utilized in silico, in vitro, and in vivo testing to model structural alterations induced by these exon 19 mutations and identify effective inhibitors. It was found that poziotinib, due to its small size and flexibility, was able to circumvent these steric changes, and is a potent and relatively selective inhibitor of the HER2 exon 19 mutant proteins. Thus, these data identify poziotinib as a potent, clinically active inhibitor of HER2 exon 19 mutations, and illuminate the molecular features of kinase inhibitors that may circumvent steric changes induced by these mutations.

Accordingly, certain embodiments of the present disclosure provide methods for treating cancer patients with HER2 exon 19 mutations, such as HER2 exon 19 point mutations. In particular, the present methods comprise the administration of poziotinib (also known as HM781-36B) to patients identified to have HER exon 19 point mutations. The size and flexibility of poziotinib overcomes steric hindrance, inhibiting HER2 exon 19 mutants at low nanomolar concentrations. Thus, poziotinib as well as structurally similar inhibitors are potent HER2 inhibitors that can be used to target HER2 exon 19 mutations which are resistant to irreversible $2^{nd}$ and $3^{rd}$ generations TKIs.

I. DEFINITIONS

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. For example, a treatment may include administration of an effective amount of poziotinib.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount," or "pharmaceutically effective amount" when used in the context of treating a patient or subject with a compound means that amount of the compound which, when administered to a subject or patient for treating or preventing a disease, is an amount sufficient to effect such treatment or prevention of the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "insertion(s)" or "insertion mutation(s)" refers to the addition of one or more nucleotide base pairs into a DNA sequence. For example, an insertion mutation of exon 19 of HER2 can occur between amino acids 668-769, of about 2-21 base pairs.

"Hybridize" or "hybridization" refers to the binding between nucleic acids. The conditions for hybridization can be varied according to the sequence homology of the nucleic acids to be bound. Thus, if the sequence homology between the subject nucleic acids is high, stringent conditions are used. If the sequence homology is low, mild conditions are used. When the hybridization conditions are stringent, the hybridization specificity increases, and this increase of the hybridization specificity leads to a decrease in the yield of non-specific hybridization products. However, under mild hybridization conditions, the hybridization specificity decreases, and this decrease in the hybridization specificity leads to an increase in the yield of non-specific hybridization products.

A "probe" or "probes" refers to a polynucleotide that is at least eight (8) nucleotides in length and which forms a hybrid structure with a target sequence, due to complementarity of at least one sequence in the probe with a sequence in the target region. The polynucleotide can be composed of DNA and/or RNA. Probes in certain embodiments, are detectably labeled. Probes can vary significantly in size. Generally, probes are, for example, at least 8 to 15 nucleotides in length. Other probes are, for example, at least 20, 30 or 40 nucleotides long. Still other probes are somewhat longer, being at least, for example, 50, 60, 70, 80, or 90 nucleotides long. Probes can be of any specific length that falls within the foregoing ranges as well. Preferably, the probe does not contain a sequence complementary to the sequence(s) used to prime for a target sequence during the polymerase chain reaction.

"Oligonucleotide" or "polynucleotide" refers to a polymer of a single-stranded or double-stranded deoxyribonucleotide or ribonucleotide, which may be unmodified RNA or DNA or modified RNA or DNA.

A "modified ribonucleotide" or deoxyribonucleotide refer to molecules that can be used in place of naturally occurring bases in nucleic acid and includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages.

A "variant" refers to a polynucleotide or polypeptide that differs relative to a wild-type or the most prevalent form in a population of individuals by the exchange, deletion, or insertion of one or more nucleotides or amino acids, respectively. The number of nucleotides or amino acids exchanged, deleted, or inserted can be 1, 2, 3, 4, 5, 6, 7, 8, 9, 10, 11, 12, 13, 14, 15, 16, 17, 18, 19, 20 or more such as 25, 30, 35, 40, 45 or 50.

A "primer" or "primer sequence" refers to an oligonucleotide that hybridizes to a target nucleic acid sequence (for example, a DNA template to be amplified) to prime a nucleic acid synthesis reaction. The primer may be a DNA oligonucleotide, a RNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 10 to about 40 nucleotides long. In certain embodiments, for example, a primer can be 10-40, 15-30, or 10-20 nucleotides long. A primer is capable of acting as a point of initiation of synthesis on a polynucleotide sequence when placed under appropriate conditions.

"Detection," "detectable" and grammatical equivalents thereof refer to ways of determining the presence and/or quantity and/or identity of a target nucleic acid sequence. In some embodiments, detection occurs amplifying the target nucleic acid sequence. In other embodiments, sequencing of the target nucleic acid can be characterized as "detecting" the target nucleic acid. A label attached to the probe can include any of a variety of different labels known in the art that can be detected by, for example, chemical or physical means. Labels that can be attached to probes may include, for example, fluorescent and luminescence materials.

"Amplifying," "amplification," and grammatical equivalents thereof refers to any method by which at least a part of a target nucleic acid sequence is reproduced in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), recombinase-polymerase amplification (RPA) (TwistDx, Cambridg, UK), and self-sustained sequence replication (3SR), including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, $3^{rd}$ Edition).

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

II. HER2 EXON 19 MUTATIONS

Figure 2:
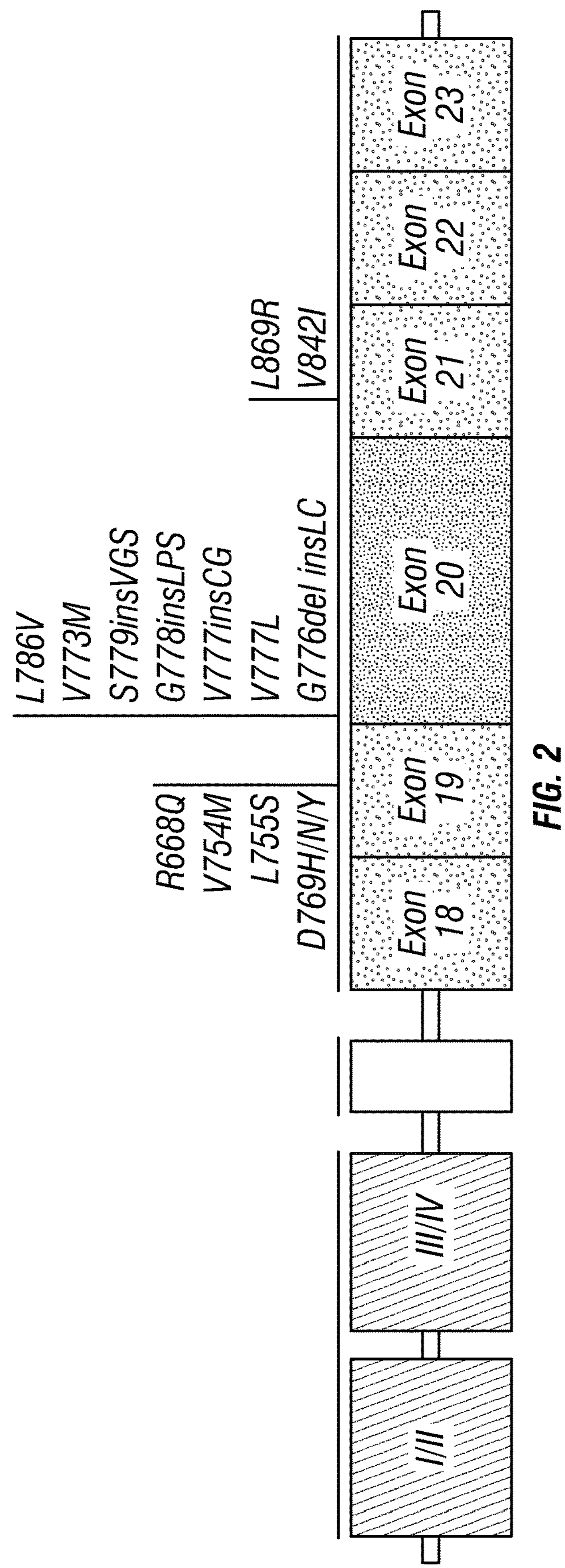
FIG. 2: Schematic depicting mutations in HER2.

Certain embodiments of the present disclosure concern determining if a subject has one or more HER2 exon 19 mutations, such as point mutations, particularly one or more mutations as depicted in FIG. 2. The subject may have 2, 3, 4, or more HER2 exon 19 mutations. Mutation detection methods are known the art including PCR analyses and nucleic acid sequencing as well as FISH and CGH. In particular aspects, the exon 19 mutations are detected by DNA sequencing, such as from a tumor or circulating free DNA from plasma.

The HER2 exon 19 mutation(s) may comprise one or more point mutations, insertions, and/or deletions of 1-18 nucleotides between amino acids 668-769. The one or more HER2 exon 19 mutations may be located at one or more residues selected from the group consisting of R668, R678, V754, L755, I767, and D769. HER2 exon 19 mutations may include R668Q, R678Q, V754M, L755P, L755S, L755W, D769H, D769N, I767M, and/or D769Y.

The patient sample can be any bodily tissue or fluid that includes nucleic acids from the lung cancer in the subject. In certain embodiments, the sample will be a blood sample comprising circulating tumor cells or cell free DNA. In other embodiments, the sample can be a tissue, such as a lung tissue. The lung tissue can be from a tumor tissue and may be fresh frozen or formalin-fixed, paraffin-embedded (FFPE). In certain embodiments, a lung tumor FFPE sample is obtained.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine, tumor, or expectorant. The sample itself will typically include nucleated cells (e.g., blood or buccal cells) or tissue removed from the subject including normal or tumor tissue. Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The presence or absence of HER2 exon 19 mutations, such as an exon 19 point mutation, as described herein can be determined using methods known in the art. For example, gel electrophoresis, capillary electrophoresis, size exclusion chromatography, sequencing, and/or arrays can be used to detect the presence or absence of mutations. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of a mutation as described herein. A mutation can be detected by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular variant.

A set of probes typically refers to a set of primers, usually primer pairs, and/or detectably-labeled probes that are used to detect the target genetic variations (e.g., HER2 exon 19 mutations) used in the actionable treatment recommendations of the present disclosure. The primer pairs are used in an amplification reaction to define an amplicon that spans a region for a target genetic variation for each of the aforementioned genes. The set of amplicons are detected by a set of matched probes. In an exemplary embodiment, the present methods may use TaqMan™ (Roche Molecular Systems, Pleasanton, Calif.) assays that are used to detect a set of target genetic variations, such as HER2 exon 19 mutations. In one embodiment, the set of probes are a set of primers used to generate amplicons that are detected by a nucleic acid sequencing reaction, such as a next generation sequencing reaction. In these embodiments, for example, AmpliSEQ™ (Life Technologies/Ion Torrent, Carlsbad, Calif.) or TruSEQ™ (Illumina, San Diego, Calif.) technology can be employed.

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., 1992), solid-phase sequencing (Zimmerman et al., 1992), sequencing with mass spectrometry such as matrix-assisted laser desorption/ionization time-of-flight mass spectrometry (MALDI-TOF/MS; Fu et al., 1998), and sequencing by hybridization (Chee et al., 1996; Drmanac et al., 1993; Drmanac et al., 1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

Other methods of nucleic acid analysis can include direct manual sequencing (Church and Gilbert, 1988; Sanger et al., 1977; U.S. Pat. No. 5,288,644); automated fluorescent sequencing; single-stranded conformation polymorphism assays (SSCP) (Schafer et al., 1995); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); denaturing high performance liquid chromatography (DHPLC, Underhill et al., 1997); infrared matrix-assisted laser desorption/ionization (IR-MALDI) mass spectrometry (WO 99/57318); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., *E. coli* mutS protein; allele-specific PCR, and combinations of such methods. See, e.g., U.S. Patent Publication No. 2004/0014095, which is incorporated herein by reference in its entirety.

In one example, a method of identifying a HER2 mutation in a sample comprises contacting a nucleic acid from said sample with a nucleic acid probe that is capable of specifically hybridizing to nucleic acid encoding a mutated HER2 protein, or fragment thereof incorporating a mutation, and detecting said hybridization. In a particular embodiment, said probe is detectably labeled such as with a radioisotope ($^{3}H$, $^{32}P$, or $^{33}P$), a fluorescent agent (rhodamine, or fluorescein) or a chromogenic agent. In a particular embodiment, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, said probes of the present disclosure are provided in a kit for identifying HER2 mutations in a sample, said kit comprising an oligonucleotide that specifically hybridizes to or adjacent to a site of mutation in the HER2 gene. The kit may further comprise instructions for treating patients having tumors that contain HER2 exon 19 mutations with poziotinib based on the result of a hybridization test using the kit.

In another aspect, a method for detecting a HER2 exon 19 mutation in a sample comprises amplifying from said sample nucleic acids corresponding to exon 19 of said or HER2 gene, or a fragment thereof suspected of containing a mutation, and comparing the electrophoretic mobility of the amplified nucleic acid to the electrophoretic mobility of corresponding wild-type HER2 gene or fragment thereof. A difference in the mobility indicates the presence of a mutation in the amplified nucleic acid sequence. Electrophoretic mobility may be determined on polyacrylamide gel.

Alternatively, nucleic acids may be analyzed for detection of mutations using Enzymatic Mutation Detection (EMD) (Del Tito et al., 1998). EMD uses the bacteriophage resolvase T4 endonuclease VII, which scans along double-stranded DNA until it detects and cleaves structural distortions caused by base pair mismatches resulting from point mutations, insertions and deletions. Detection of two short fragments formed by resolvase cleavage, for example by gel electrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed. However, EMD scanning does not identify particular base changes that occur in mutation positive samples requiring additional sequencing procedures to identity of the mutation if necessary. CEL I enzyme can be used similarly to resolvase T4 endonuclease VII as demonstrated in U.S. Pat. No. 5,869,245.

III. METHODS OF TREATMENT

Further provided herein are methods for treating or delaying progression of cancer in an individual comprising administering to the individual an effective amount of poziotinib or a structurally similar inhibitor, to a subject determined to have a HER2 exon 19 mutation, such as an exon 19 point mutation. The subject may have more than one HER exon 19 mutations.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. In particular aspects, the cancer is non-small cell lung cancer.

In some embodiments, the subject is a mammal, e.g., a primate, preferably a higher primate, e.g., a human (e.g., a patient having, or at risk of having, a disorder described herein). In one embodiment, the subject is in need of enhancing an immune response. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

Certain embodiments concern the administration of poziotinib (also known as HM781-36B, HM781-36, and 1-[4-[4-(3,4-dichloro-2-fluoroanilino)-7-methoxyquinazolin-6-yl]oxypiperidin-1-yl]prop-2-en-1-one) to a subject determined to have HER2 exon 19 mutations, such as an exon 19 point mutation. Poziotinib is a quinazoline-based pan-HER inhibitor that irreversibly blocks signaling through the HER family of tyrosine-kinase receptors including HER1, HER2, and HER4. Poziotinib or structurally similar compounds (e.g., U.S. Pat. No. 8,188,102 and U.S. Patent Publication No. 20130071452; incorporated herein by reference) may be used in the present methods.

A. Pharmaceutical Compositions

Also provided herein are pharmaceutical compositions and formulations comprising poziotinib and a pharmaceutically acceptable carrier for subjects determined to have a HER2 exon 19 mutation, such as an exon 19 point mutation.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve poziotinib in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

The poziotinib may be administered before, during, after, or in various combinations relative to an additional cancer therapy, such as immune checkpoint therapy. The administrations may be in intervals ranging from concurrently to minutes to days to weeks. In embodiments where the poziotinib is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below poziotinib is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine;

acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129; International Patent Publication Nos. WO 01/14424, WO 98/42752, and WO 00/37504 (CP675,206, also known as tremelimumab; formerly ticilimumab); U.S. Pat. No. 6,207,156; Hurwitz et al., 1998; Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application Nos. WO2001014424, and WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. KIT

Also within the scope of the present disclosure are kits for detecting HER2 exon 19 mutations, such as those disclosed herein. An example of such a kit may include a set of exon 19 mutation-specific primers. The kit may further comprise instructions for use of the primers to detect the presence or absence of the specific HER2 exon 19 mutations described herein. The kit may further comprise instructions for diagnostic purposes, indicating that a positive identification of HER2 exon 19 mutations described herein in a sample from a cancer patient indicates sensitivity to the tyrosine kinase inhibitor poziotinib or a structurally similar inhibitor. The kit may further comprise instructions that indicate that a positive identification of HER2 exon 19 mutations described herein in a sample from a cancer patient indicates that a patient should be treated with poziotinib or a structurally similar inhibitor.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of Drugs for Cancer Cells with HER Exon 19 Mutations Ba/F3 cells expressing exon 19 point mutation L755P were generated. The cells were tested for IL-3 independence and screened against HER2 TKIs including lapatinib, afatinib, EGF-816, ibrutinib, and poziotinib, as well as the HER2 antibody trastuzumab using the Cell Titer Glo assay. Ba/F3 cells expressing HER2 L755P were found to grow independent of IL-3, indicating that HER2 L755P is an activating mutation. In addition, trastuzumab, lapatinib, EGF-816, and ibrutinib failed to inhibit cell viability of Ba/F3 cells expressing HER2 L755P protein.

Figure 3:
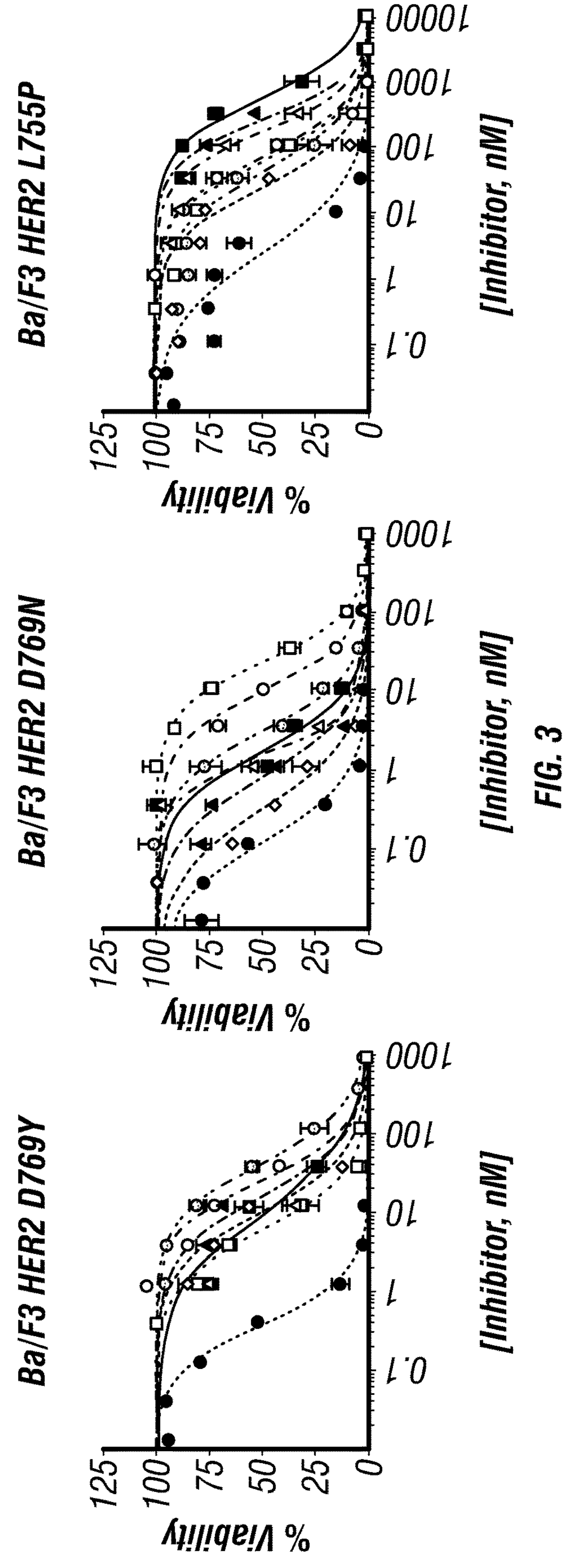
FIG. 3: Dose response curves of cell viability of HER2 mutant Ba/F3 cell lines treated with poziotinib or indicated TKIs for 72 hours.
Figure 3:
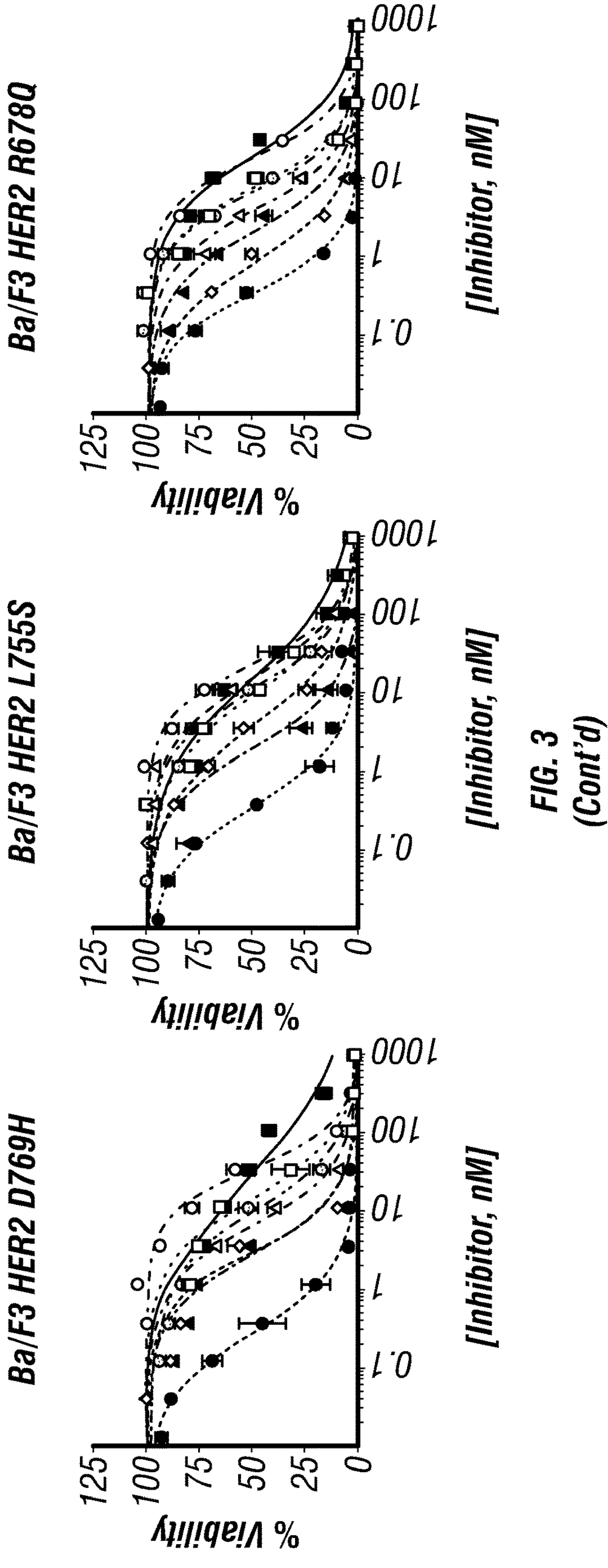

Although 2nd generation TKI afatinib showed some activity (IC50 value=13 nM), it was found that poziotinib significantly inhibited the growth of Ba/F3 HER2 L755P mutant cells with an IC50 value of 3.0 nM. In addition, several other HER2 exon 19 mutations including D769Y, D769N, D769H, L755S, and R678Q were tested for their sensitivity to different TKIs including poziotinib. It was found that poziotinib inhibited the growth of these mutant cells (FIG. 3).

Figure 4:
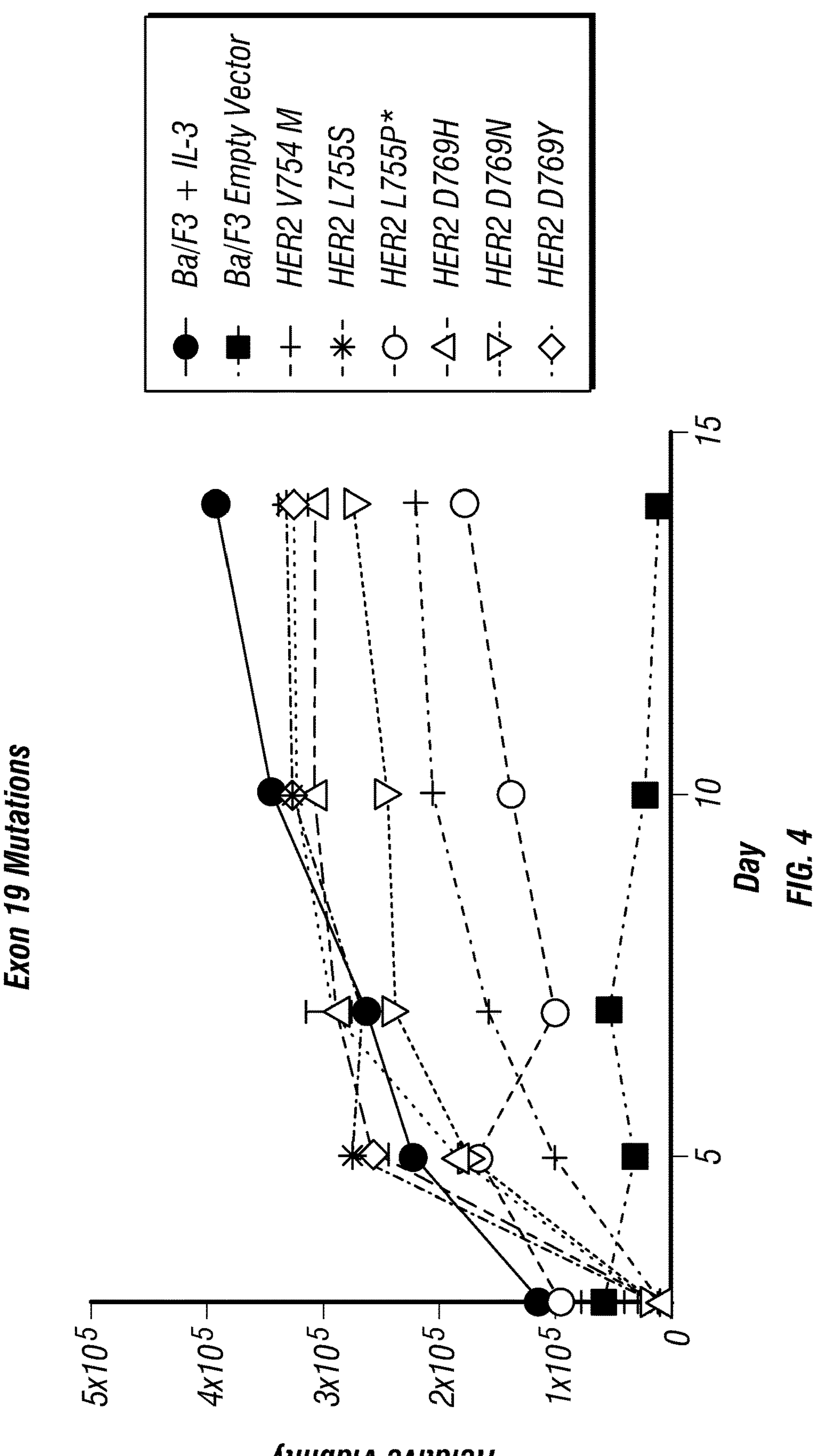
FIG. 4: Cell viability of stable Ba/F3 cell lines expressing HER2 exon 19 mutations grown in IL-3 free conditions for 14 days. Cell viability was determined every 3 days by the Cell Titer Glo assay. The mean±SEM is plotted for each cell line (n=3 biologically independent experiments).
Figure 5A:
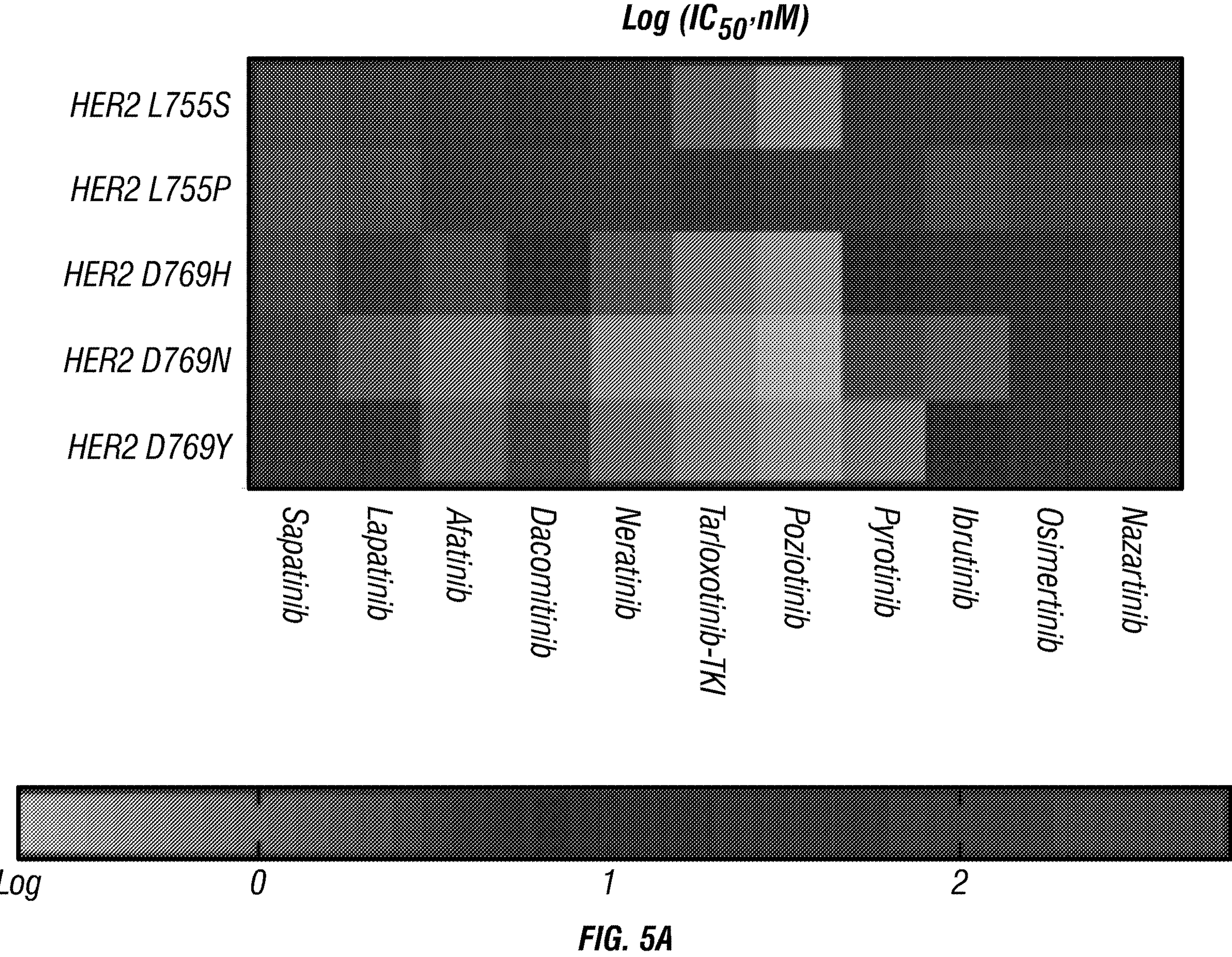
Figure 5B:
Figure 5B:
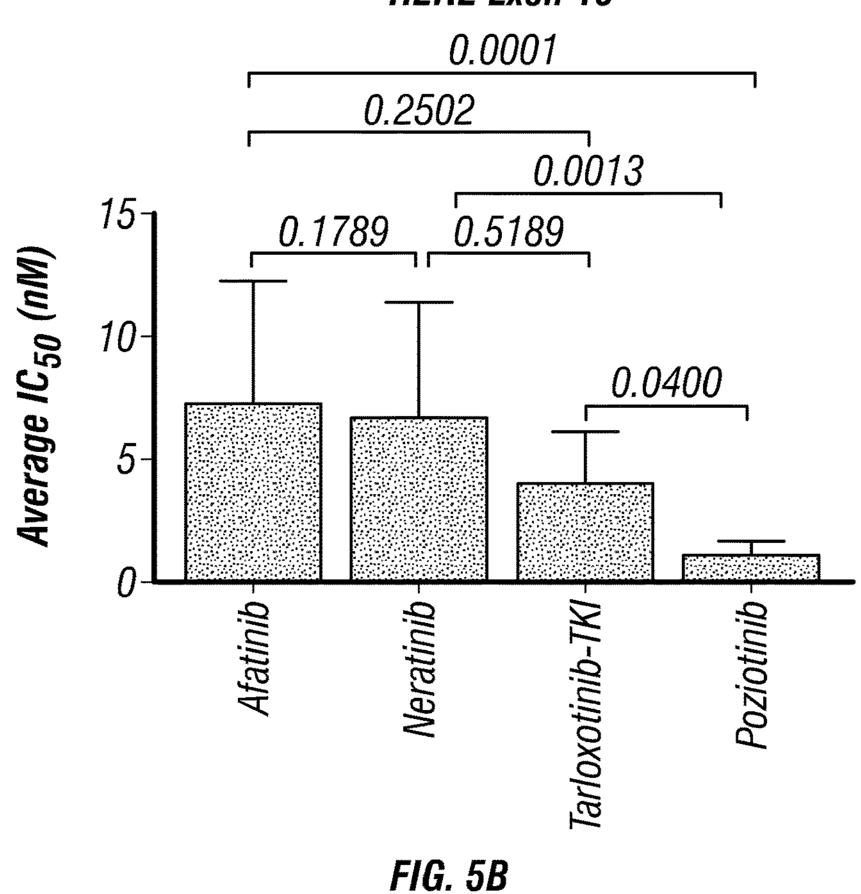
Figure 5C:
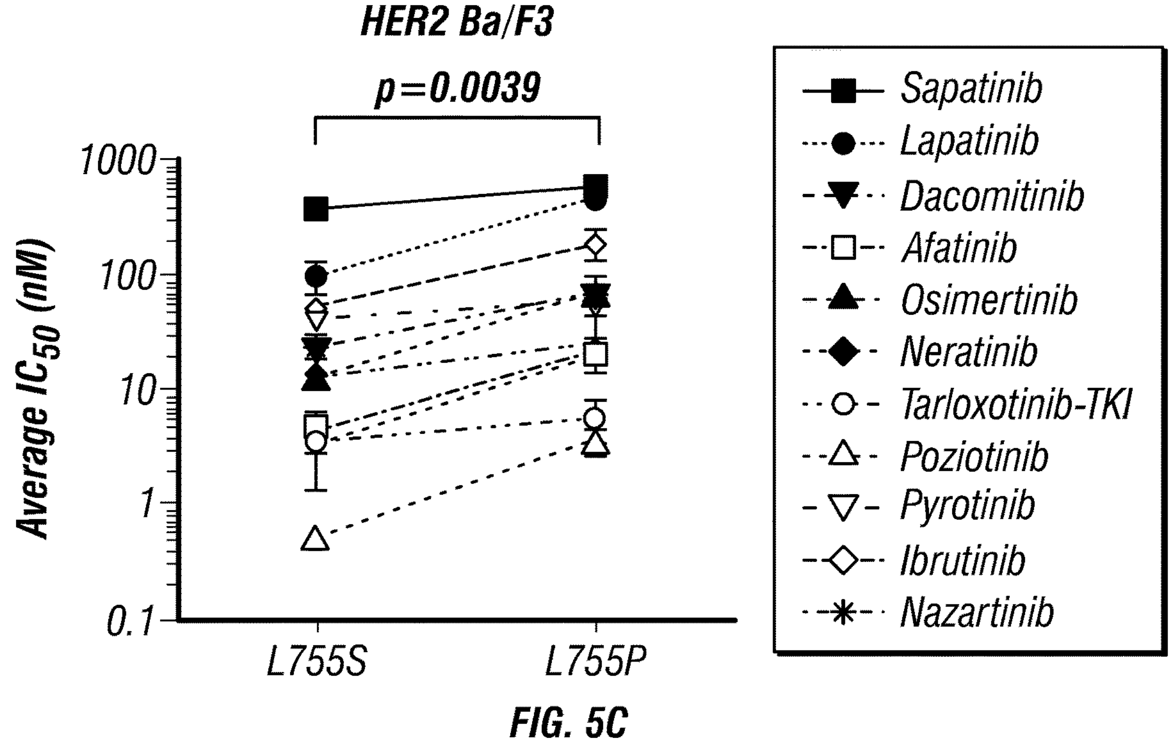

Cell viability of stable Ba/F3 cell lines expressing HER2 exon 19 mutations grown in IL-3 free conditions was measured for 14 days. Cell viability was determined every 3 days by the Cell Titer Glo assay (FIG. 4). FIG. 5A shows a heatmap of log $IC_{50}$ values of Ba/F3 cells stably expressing the indicated mutations after 72 hours of drug treatment. Average $IC_{50}$ values of Ba/F3 cells expressing L755S or L755P with indicated inhibitors were measured (FIG. 5C). It was observed that treatment with poziotinib had the lowest $IC_{50}$ values as compared to the other inhibitors tested.

Figure 6A:
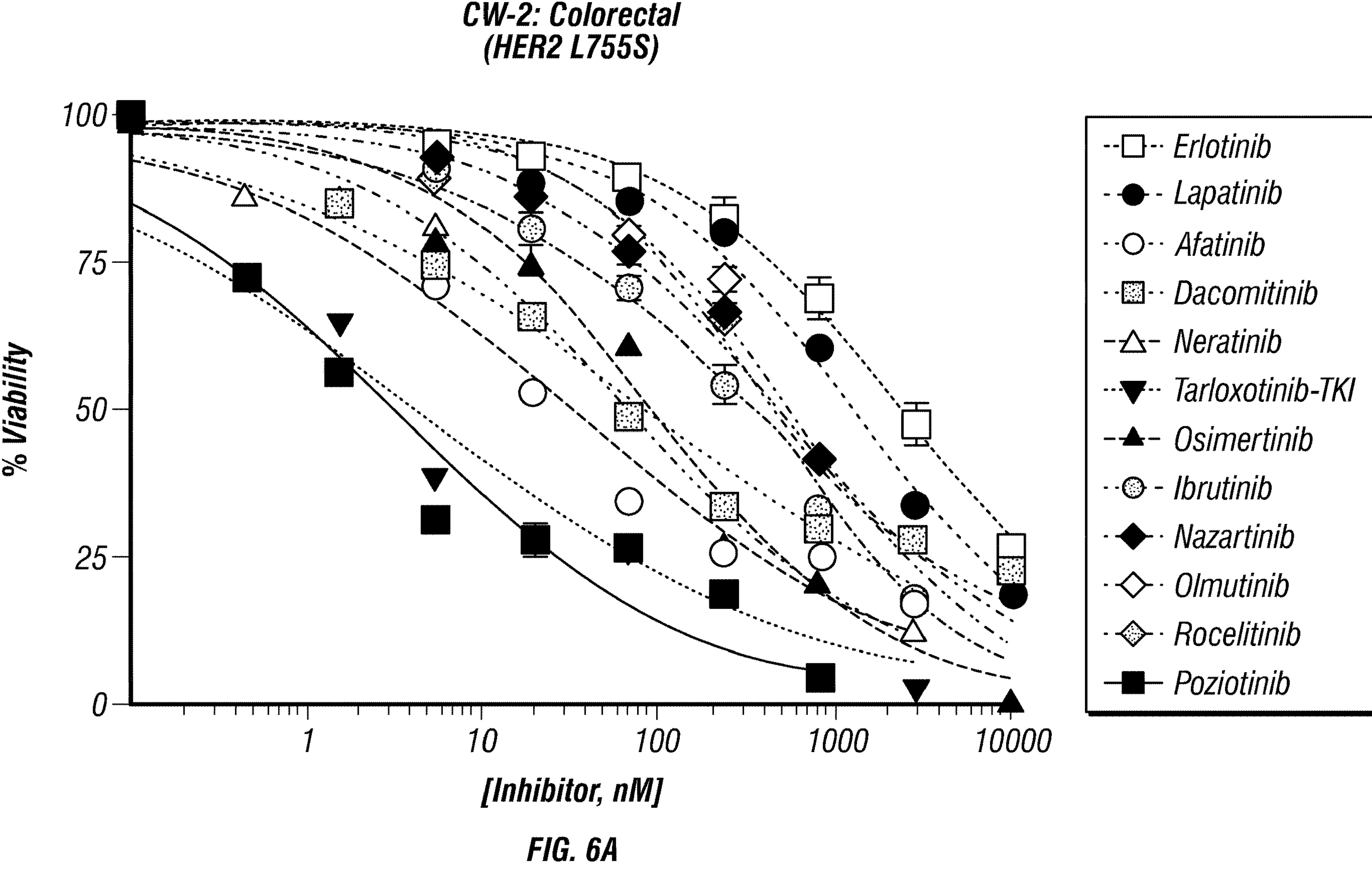
FIGS. 6A-6C: (A) Dose response curves of CW-2 cells treated with indicated inhibitors for 72 hours. (B) Tumor growth curve of CW-2 cells (HER2 L755S) xenografts treated with indicated inhibitors. Two-Way ANOVA was used to determine statistical significance. Asterisk indicate significance between vehicle and poziotinib or neratinib. (C) Bar graph of CW-2 tumor volume at day 21. Dots are representative of individual tumors, and bars are representative of mean±SEM. The dotted line indicates randomization at 350 $mm^3$ Statistical significance was determined by one-way ANOVA.

In further experiments, CW-2 colorectal cells were treated with the different inhibitors at various concentrations and poziotinib was shown to result in the highest decrease in cell viability (FIG. 6A). A mouse study was performed with mice inoculated with CW-2 cells treated with poziotinib, afatinib, or neratinib. Tumor growth was significantly decreased in the mice treated with poziotinib at 5 mg/kg (FIG. 6C). Thus, poziotinib, as well as structurally similar inhibitors, are potent inhibitors of HER2 exon 19 mutations and can be used as therapeutics to overcome de novo drug resistance.

Example 2—Materials and Methods

Cell line generation and IL-3 deprivation: Ba/F3 cell line, was cultured in complete RPMI-1640 (R8758; Sigma Life Science) media supplemented with L-glutamine, 10% heat inactivated FBS (Gibco), 1% penicillin/streptomycin (Sigma Life Science), and 10 ng/ml mouse IL-3 (R&D systems) under sterile conditions. Stable cell lines were generated by retroviral transduction of Ba/F3 cell line for 12 hours. Retroviruses were generated by transfecting pBabe-Puro based vectors into the Phoenix 293T ampho packing cell line (Orbigen) using Lipofectamine 2000 (Invitrogen). 72 hours after transduction, 2 μg/ml puromycin (Invitrogen) was added to the media. After 5 days of selection, cells were stained with FITC-HER2 (Biolegend) and sorted via FACS. Cell lines were then grown in the absence of IL-3 for 15 days and cell viability was determined every 3 days using the Cell Titer Glo assay (Progema). Resulting stable cell lines were maintained in complete RPMI-1640 media described above without IL-3. Cell line identity was confirmed by DNA fingerprinting via short tandem repeats using the PowerPlex 1.2 kit (Promega). Fingerprinting results were compared with reference fingerprints maintained by the primary source of the cell line. All cell lines were free of *mycoplasma*. To generate HER2 L775P cell lines, cells were transduced with c.2264T>C (created from Bioinnovatise from pBabe-puro HER WT from Addgene (#40978)).

TABLE 1

Figure 6B:
Figure 6B:
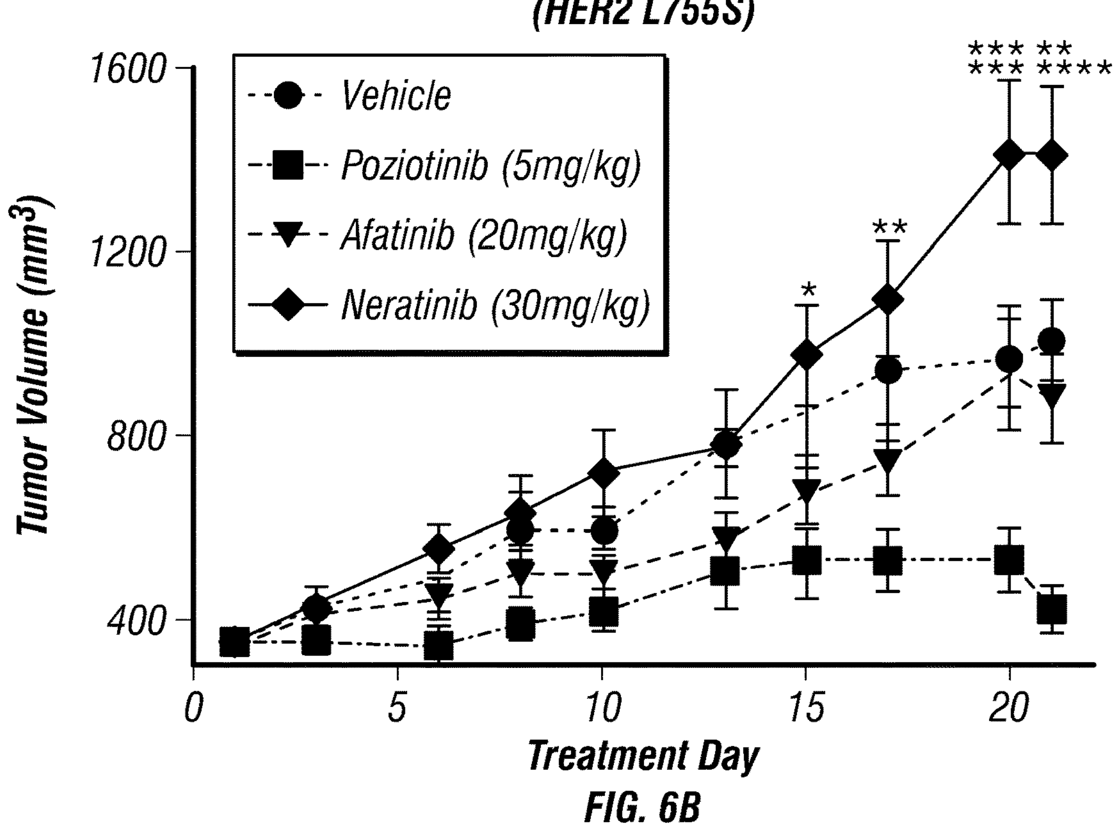
Figure 6C:
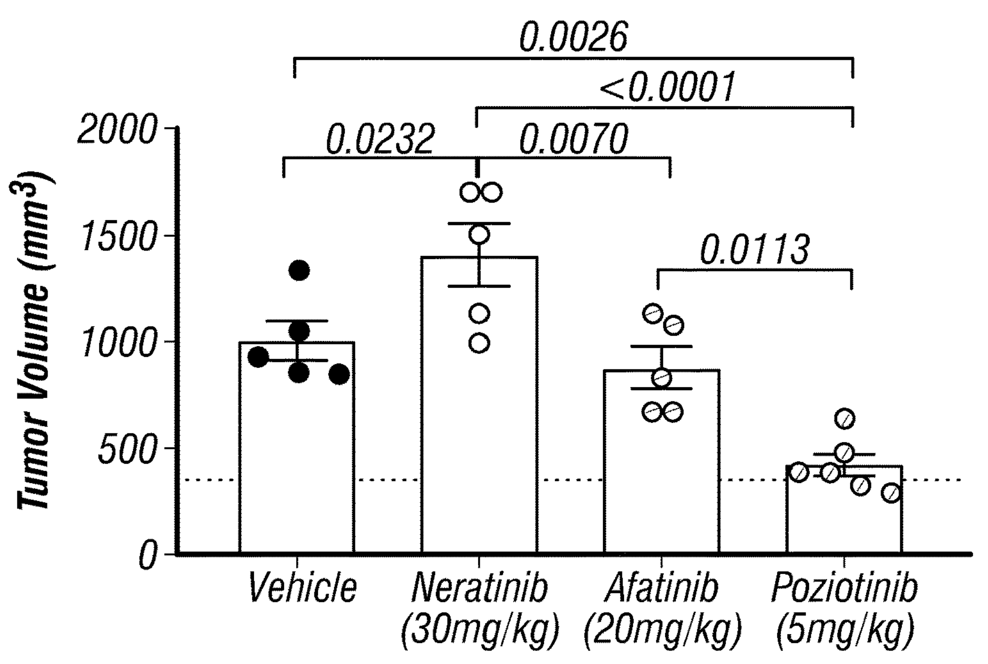

Statistics for two-way ANOVA of FIG. 6B.

| Tukey's multiple comparisons test | Summary | Adjusted P Value |
|---|---|---|
| Day 10 | | |
| Vehicle vs. Poziotinib (5 mg/kg) | ns | 0.3888 |
| Vehicle vs. Afatinib (20 mg/kg) | ns | 0.8492 |
| Vehicle vs. Neratinib (30 mg/kg) | ns | 0.8826 |
| Poziotinib (5 mg/kg) vs. Afatinib (20 mg/kg) | ns | 0.0809 |
| Poziotinib (5 mg/kg) vs. Neratinib (30 mg/kg) | * | 0.0333 |
| Afatinib (20 mg/kg) vs. Neratinib (30 mg/kg) | ns | 0.2222 |
| Day 13 | | |
| Vehicle vs. Poziotinib (5 mg/kg) | ns | 0.067 |
| Vehicle vs. Afatinib (20 mg/kg) | ns | 0.2563 |
| Vehicle vs. Neratinib (30 mg/kg) | ns | 0.9896 |
| Poziotinib (5 mg/kg) vs. Afatinib (20 mg/kg) | ns | 0.9266 |
| Poziotinib (5 mg/kg) vs. Neratinib (30 mg/kg) | ns | 0.0767 |
| Afatinib (20 mg/kg) vs. Neratinib (30 mg/kg) | ns | 0.3041 |
| Day 15 | | |
| Vehicle vs. Poziotinib (5 mg/kg) | * | 0.0152 |
| Vehicle vs. Afatinib (20 mg/kg) | ns | 0.391 |
| Vehicle vs. Neratinib (30 mg/kg) | ns | 0.7201 |
| Poziotinib (5 mg/kg) vs. Afatinib (20 mg/kg) | ns | 0.5209 |
| Poziotinib (5 mg/kg) vs. Neratinib (30 mg/kg) | *** | 0.0003 |
| Afatinib (20 mg/kg) vs. Neratinib (30 mg/kg) | * | 0.0452 |
| Day 17 | | |
| Vehicle vs. Poziotinib (5 mg/kg) | ** | 0.0012 |
| Vehicle vs. Afatinib (20 mg/kg) | ns | 0.3219 |
| Vehicle vs. Neratinib (30 mg/kg) | ns | 0.5028 |
| Poziotinib (5 mg/kg) vs. Afatinib (20 mg/kg) | ns | 0.193 |
| Poziotinib (5 mg/kg) vs. Neratinib (30 mg/kg) | **** | <0.001 |
| Afatinib (20 mg/kg) vs. Neratinib (30 mg/kg) | * | 0.0116 |

TABLE 1-continued

Statistics for two-way ANOVA of FIG. 6B.

| Tukey's multiple comparisons test | Summary | Adjusted P Value |
|---|---|---|
| Day 20 | | |
| Vehicle vs. Poziotinib (5 mg/kg) | *** | 0.0005 |
| Vehicle vs. Afatinib (20 mg/kg) | ns | 0.0896 |
| Vehicle vs. Neratinib (30 mg/kg) | *** | 0.0007 |
| Poziotinib (5 mg/kg) vs. Afatinib (20 mg/kg) | ** | 0.0015 |
| Poziotinib (5 mg/kg) vs. Neratinib (30 mg/kg) | **** | <0.0001 |
| Afatinib (20 mg/kg) vs. Neratinib (30 mg/kg) | *** | 0.0002 |
| Day 21 | | |
| Vehicle vs. Poziotinib (5 mg/kg) | **** | <0.0001 |
| Vehicle vs. Afatinib (20 mg/kg) | ns | 0.6386 |
| Vehicle vs. Neratinib (30 mg/kg) | ** | 0.0029 |
| Poziotinib (5 mg/kg) vs. Afatinib (20 mg/kg) | *** | 0.0003 |
| Poziotinib (5 mg/kg) vs. Neratinib (30 mg/kg) | **** | <0.0001 |
| Afatinib (20 mg/kg) vs. Neratinib (30 mg/kg) | **** | <0.0001 |

Cell viability assay and $IC_{50}$ estimation: Cell viability was determined using the Cell Titer Glo assay (Promega) as previously described (Robichaux et al., 2018). Briefly, 2000-3000 cells per well were plated in 384-well plates (Greiner Bio-One) in technical triplicate. Cells were treated with seven different concentrations of tyrosine kinase inhibitors or vehicle alone at a final volume of 40 μL per well. After 3 days, 11 μL of Cell Titer Glo was added to each well. Plates were shaken for 15 minutes, and bioluminescence was determined using a FLUOstar OPTIMA multi-mode micro-plate reader (BMG LABTECH). Bioluminescence values were normalized to DMSO treated cells, and normalized values were plotted in GraphPad Prism using non-linear regression fit to normalized data with a variable slope. $IC_{50}$ values were calculated by GraphPad Prism at 50% inhibition.

Tyrosine kinase inhibitors and T-DM1: All inhibitors were purchased from Selleck Chemical with the exception of EGF816 and pyrotinib which were purchased from MedChem Express. All inhibitors were dissolved in DMSO at a concentration of 10 mM and stored at −80° C. Inhibitors were limited to two freeze thaw/cycle before being discarded. T-DM1 was purchased reconstituted from the M.D. Anderson Cancer Center institutional pharmacy.

Human cell lines: MCF10A cells were purchased from ATCC and were cultured in DMEM/F12 media supplemented with 1% penicillin/streptomycin, 5% horse serum (sigma), 20 ng/ml EGF, 0.5 mg/ml hydrocortisone, and 10 ug/ml insulin. Stable cell lines were created by retroviral transduction, and retroviruses were generated by transfecting pBabe-Puro based vectors summarized in Table 1 (Addgene and Bioinnovatise) into Phoenix 293T-ampho cells (Orbigen) using Lipofectamine 2000 (Invitrogen). Two days after transduction, 0.5 μg/ml puromycin (Invitrogen) was added to the RPMI media. After 14 days of selection, cells were tested in cell viability assays as described above. CW-2 cells were provided by the Riken cell line database under MTA, and were maintained in RPMI containing 10% FBS and 1% penicillin/streptomycin.

In vivo xenograft studies: CW-2 cell line xenografts were created by injecting $1\times10^6$ cells in 50% matrigel into 6-week-old female nu/nu nude mice. When tumors reached 350 $mm^3$ mice were randomized into 4 groups: 20 mg/kg afatinib, 5 mg/kg poziotinib, 30 mg/kg neratinib, or vehicle control (0.5% Methylcellulose, 2% Tween-80 in dH2O). Tumor volumes were measured three times per week. Mice received drug Monday-Friday (5 days per week), but began dosing on Wednesday allowing for a 2-day holiday after the first 3 days of dosing.

Y772dupYVMA PDX mice were purchased from Jax Labs (Model #TM01446). Fragments from tumors expressing HER2 Y772dupYVMA were inoculated into 5- to 6-week old female NSG mice (Jax Labs #005557). Mice were measured three times per week, and when tumors reached a volume of 200-300 $mm^3$ mice were randomized into four treatment groups: vehicle control (0.5% Methylcellulose, 0.05% Tween-80 in dH2O), 2.5 mg/kg poziotinib, 10 mg/kg T-DM1, or combination of 2.5 mg/kg poziotinib and 10 mg/kg T-DM1. Tumor volumes and body weight were measured three times per week. Mice treated with 2.5 mg/kg poziotinib received drug orally Monday-Friday (5 days per week). Mice treated with 10 mg/kg T-DM1 received one intravenous (IV) dose of T-DM1 on the day of randomization. Mice treated with combination poziotinib and T-DM1 received one IV dose of T-DM1 and began 2.5 mg/kg poziotinib five days per week, 3 days after the dose of T-DM1. Mice received a holiday from dosing if the mouse dropped in body weight by greater than 10% or if body weight dropped below 20 grams. Progression free survival was defined as tumor doubling from best response for two consecutive measurements. Complete regression was defined as greater than 95% reduction in tumor burden, and for mice with complete regression, tumor doubling was defined greater than 75 $mm^3$ for more than two consecutive measurements. Experiments were completed in agreement with Good Animal Practices and with approval from MD Anderson Cancer Center Institutional Animal Care and Use Committee (Houston, TX).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcila et al., *Clin Cancer Res* 18:4910-8, 2012.
Arcila et al., *Mol Cancer Ther* 12(2):220-229, 2013.
Austin-Ward and Villaseca, *Revista Medica de Chile,* 126 (7):838-845, 1998.
Ausubel et al., Current Protocols in Molecular Biology, John Wiley & Sons, New York, NY, 2003.
Bukowski et al., *Clinical Cancer Res.,* 4(10):2337-2347, 1998.
Camacho et al. *J Clin Oncology* 22(145): Abstract No. 2505 (antibody CP-675206), 2004.
Cha et al. *Int J Cancer* 130:2445-54, 2012.
Chee et al., *Science,* 274:610-614, 1996.
Cho et al., *Cancer Res* 73:6770-9, 2013.
Christodoulides et al., *Microbiology,* 144(Pt 11):3027-3037, 1998.
Church and Gilbert, *Proc. Natl. Acad. Sci. USA* 81:1991-1995 (1988).
Cotton et al., *Proc. Natl. Acad. Sci. USA* 85:4397-4401 (1985).
Davidson et al., *J. Immunother.,* 21(5):389-398, 1998.
Davies et al., *Plos One* 8, 2013.
Del Tito et al., *Clinical Chemistry* 44:731-739, 1998.
Drmanac et al., *Nat. Biotechnol.,* 16:54-58, 1998.
Drmanac et al., *Science,* 260:1649-1652, 1993.
Flavell et al., Cell 15:25 (1978).
Fu et al., *Nat. Biotechnol.,* 16:381-384, 1998/Geever et al., *Proc. Natl. Acad. Sci. USA* 78:5081 (1981).
Hanibuchi et al., *Int. J. Cancer,* 78(4):480-485, 1998.
Hellstrand et al., *Acta Oncologica,* 37(4):347-353, 1998.
Hollander, *Front. Immun.,* 3:3, 2012.
Hong et al., *J Biol Chem* 282:19781-7, 2007.
Hui and Hashimoto, *Infection Immun.,* 66(11):5329-5336, 1998.
Hurwitz et al. *Proc Natl Acad Sci USA* 95(17): 10067-10071, 1998.
International Patent Publication No. WO 99/57318
International Patent Publication No. WO1995001994
International Patent Publication No. WO1998042752
International Patent Publication No. WO2000037504
International Patent Publication No. WO2001014424
International Patent Publication No. WO2009/101611
International Patent Publication No. WO2009/114335
International Patent Publication No. WO2010/027827
International Patent Publication No. WO2011/066342
International Patent Publication No. WO2015016718
International Patent Publication No. WO 00/37504
International Patent Publication No. WO01/14424
International Patent Publication No. WO98/42752
Kosaka et al., *Cancer Res* 2017.
Leal, M., *Ann N Y Acad Sci* 1321, 41-54, 2014.
Lynch et al., *N Engl J Med.* 350(21):2129-2139, 2004.
Maemondo et al., *N Engl J Med* 362:2380-8, 2010.
Mitsudomi and Yatabe, *Cancer Sci.* 98(12):1817-1824, 2007.
Mokyr et al. *Cancer Res* 58:5301-5304, 1998.
Oxnard et al., *J Thorac Oncol.* 8(2):179-184, 2013.
Paez et al., *Science* 304(5676):1497-1500, 2004.
Pao et al., *Proc Nall Acad Sci USA* 101(36):13306-13311, 2004.
Pardoll, *Nat Rev Cancer,* 12(4): 252-64, 2012.
Perera et al., *Proc Natl Acad Sci USA* 106:474-9, 2009.
Qin et al., *Proc. Natl. Acad. Sci. USA,* 95(24):14411-14416, 1998.
Raca et al., *Genet Test* 8(4):387-94 (2004).
Robichaux et al., *Nature Medicine,* 2018.
Sanger et al., *Proc. Natl. Acad. Sci. USA* 74:5463-5467 (1977).
Sears et al., *Biotechniques,* 13:626-633, 1992.
Sheffield et al., *Proc. Natl. Acad. Sci. USA* 86:232-236 (1989).
Shen et al., *J Recept Signal Transduct Res* 36:89-97, 2016.
Thress et al., *Nat Med* 21:560-2, 2015.
U.S. Pat. No. 4,870,287
U.S. Pat. No. 5,288,644
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,869,245

U.S. Pat. No. 5,885,796
U.S. Pat. No. 6,207,156
U.S. Pat. No. 8,008,449
U.S. Pat. No. 8,017,114
U.S. Pat. No. 8,119,129
U.S. Pat. No. 8,188,102
U.S. Pat. No. 8,329,867
U.S. Pat. No. 8,354,509
U.S. Pat. No. 8,735,553
U.S. Patent Publication No. 2004/0014095
U.S. Patent Publication No. 2005/0260186
U.S. Patent Publication No. 2006/0104968
U.S. Patent Publication No. 20110008369
U.S. Patent Publication No. 20130071452
U.S. Patent Publication No. 2014022021
U.S. Patent Publication No. 20140294898
Underhill et al., *Genome Res.* 7:996-1005 (1997).
Yang et al., *Int J Cancer* 2016.
Yasuda et al., *Sci Transl Med* 5(216):216ra177, 2013.
Zimmerman et al., *Methods Mol. Cell. Biol.,* 3:39-42, 1992.

5. The method of claim 1, wherein the subject was determined to have an HER2 exon 19 mutation by analyzing a genomic sample from the subject.

6. The method of claim 1, wherein the presence of an HER2 exon 19 mutation is determined by nucleic acid sequencing or PCR analyses.

7. The method of claim 1, further comprising administering an additional anti-cancer therapy.

8. The method of claim 7, wherein the additional anti-cancer therapy is chemotherapy, radiotherapy, gene therapy, surgery, hormonal therapy, anti-angiogenic therapy or immunotherapy.

9. The method of claim 7, wherein the poziotinib and/or anti-cancer therapy are administered intravenously, subcutaneously, intraosseously, orally, transdermally, in a sustained release formulation, in a controlled release formulation, in a delayed release formulation, as a suppository, or sublingually.

10. The method of claim 7, wherein administering the poziotinib and/or anti-cancer therapy comprises local, regional or systemic administration.

The invention claimed is:

1. A method of treating cancer in a subject comprising administering an effective amount of poziotinib to the subject, wherein the subject has been determined to have HER2 genetic variations consisting of one or more HER2 exon 19 mutations at one or more residues selected from the group consisting of R678, L755 and D769, and wherein the cancer is non-small cell lung cancer or colorectal cancer.

2. The method of claim 1, wherein the one or more HER2 exon 19 mutations are at one or more residues selected from the group consisting of R678, and D769.

3. The method of claim 1, wherein the one or more HER2 exon 19 mutations are selected from the group consisting of R678Q, L755P, L755W, D769H, D769N, and D769Y.

4. The method of claim 1, wherein the exon 19 mutation is L755P or R678Q.

11. The method of claim 1, wherein the poziotinib is administered orally.

12. The method of claim 1, wherein the poziotinib is administered at a dose of 5-25 mg.

13. The method of claim 1, wherein the poziotinib is administered at a dose of 8 mg, 12 mg, or 16 mg.

14. The method of claim 1, wherein the poziotinib is administered daily.

15. The method of claim 14, wherein the poziotinib is administered on a continuous basis.

16. The method of claim 14, wherein the poziotinib is administered on 28 day cycles.

17. The method of claim 1, wherein the cancer is non-small cell lung cancer (NSCLC).

18. The method of claim 1, wherein the cancer is colorectal cancer.

* * * * *